US008834858B2

(12) United States Patent
Ledwidge et al.

(10) Patent No.: US 8,834,858 B2
(45) Date of Patent: Sep. 16, 2014

(54) TREATMENT FOR DYSLIPIDEMIA

(75) Inventors: Mark Ledwidge, Douglas (IE); Pat O'Flynn, Douglas (IE); John Gilmer, Tallaght (IE)

(73) Assignee: Solvotrin Therapeutics Ltd., Cork (IE)

( * ) Notice: Subject to any disclaimer, the term of this patent is extended or adjusted under 35 U.S.C. 154(b) by 0 days.

(21) Appl. No.: 13/175,700

(22) Filed: Jul. 1, 2011

(65) Prior Publication Data

US 2012/0082634 A1   Apr. 5, 2012

(51) Int. Cl.
| | |
|---|---|
| A61K 31/455 | (2006.01) |
| A61K 31/616 | (2006.01) |
| A61K 31/60 | (2006.01) |
| A61K 31/625 | (2006.01) |
| A61K 31/785 | (2006.01) |
| A61P 3/06 | (2006.01) |
| A61P 7/00 | (2006.01) |
| A61P 3/10 | (2006.01) |
| A61K 31/40 | (2006.01) |
| A61K 31/404 | (2006.01) |
| A61K 31/192 | (2006.01) |
| A61K 31/22 | (2006.01) |
| A61K 45/06 | (2006.01) |
| A61K 31/216 | (2006.01) |
| A61K 31/366 | (2006.01) |
| A61K 31/505 | (2006.01) |
| A61K 31/401 | (2006.01) |

(52) U.S. Cl.
CPC .............. *A61K 31/505* (2013.01); *A61K 31/40* (2013.01); *A61K 31/404* (2013.01); *A61K 31/192* (2013.01); *A61K 31/22* (2013.01); *A61K 31/455* (2013.01); *A61K 31/785* (2013.01); *A61K 45/06* (2013.01); *A61K 31/216* (2013.01); *A61K 31/366* (2013.01); *A61K 31/401* (2013.01); *A61K 31/616* (2013.01); *A61K 31/60* (2013.01)
USPC ......... 424/78.01; 514/160; 514/165; 514/167

(58) Field of Classification Search
USPC ................... 514/166, 165, 163, 161
See application file for complete search history.

(56) References Cited

U.S. PATENT DOCUMENTS

| 6,469,035 B1 * | 10/2002 | Cefali ............................ 514/356 |
| 7,374,779 B2 * | 5/2008 | Chen et al. .................... 424/451 |
| 2009/0186091 A1 * | 7/2009 | Darlington, Jr. .............. 424/489 |

FOREIGN PATENT DOCUMENTS

| WO | WO 2009/080795 | 7/2009 |
| WO | WO-2009080795 A1 | 7/2009 |

OTHER PUBLICATIONS

International Search Report for PCT/IB2011/002285 (Publication No. WO 2012/017321) dated Feb. 9, 2012.
Written Opinion for PCT/IB2011/002285 (Publication No. WO 2012/017321) dated Feb. 9, 2012.
Akaike et al., "Effect of Aspirin Treatment on Serum Concentrations of Lipoprotein(a) in Patients with Atherosclerotic Diseases", *Clinical Chemistry*, vol. 48(9); 1454-1459 (2002).
Davidson et al., "Niacin Use and Cutaneous Flushing: Mechanisms and Strategies for Prevention", *The American Journal of Cardiology*, vol. 101(8): S14-S19 (2008).
Davies et al., "Salicylates targeting insulin resistance", *Drugs of the Future*, vol. 32(4): 361-365 (2007).
Abbott Laboratory Ireland Limited (2009). Summary of Product Characteristics: Niaspan, Medicines.
Antithrombotic Trialists Colloboration (2002). "Collaborative meta-analysis of randomised trials of antiplatelet therapy for prevention of death, myocardial infarction, and stroke in high risk patients." *BMJ* 324(7329): 71-86.
Antithrombotic Trialists, C. (2009). "Aspirin in the primary and secondary prevention of vascular disease: collaborative meta-analysis of individual participant data from randomised trials." *The Lancet* 373(9678): 1849-1860.
Avorn, J., J. Monette, et al. (1998). "Persistence of Use of Lipid-Lowering Medications." *JAMA: The Journal of the American Medical Association* 279(18): 1458-1462.
Baigent, C. (2005). "Efficacy and safety of cholesterol-lowering treatment: prospective meta-analysis of data from 90056 participants in 14 randomised trials of statins." *The Lancet* 366(9493): 1267-1278.
Barter, P. J., M. Caulfield, et al. (2007). "Effects of Torcetrapib in Patients at High Risk for Coronary Events." *N Engl J Med* 357(21): 2109-2122.
Benner, J. S., R. J. Glynn, et al. (2002). "Long-term Persistence in Use of Statin Therapy in Elderly Patients." *JAMA: The Journal of the American Medical Association* 288(4): 455-461.
Brown, B. G., X.-Q. Zhao, et al. (2001). "Simvastatin and Niacin, Antioxidant Vitamins, or the Combination for the Prevention of Coronary Disease." *N Engl J Med* 345(22): 1583-1592.
Campbell, C. L., S. Smyth, et al. (2007). "Aspirin Dose for the Prevention of Cardiovascular Disease: A Systematic Review." *JAMA* 297(18): 2018-2024.
Canner, P. L., K. G. Berge, et al. (1986). "Fifteen year mortality in Coronary Drug Project patients: long-term benefit with niacin." *JACC* 6: 1245-1255.
Capuzzi, D., J. Morgan, et al. (2000). "Niacin dosing: Relationship to benefits and adverse effects." *Current Atherosclerosis Reports* 2(1): 64-71.
Castelli, W. P., R. J. Garrison, et al. (1986). "Incidence of Coronary Heart Disease and Lipoprotein Cholesterol Levels: The Framingham Study." *JAMA* 256(20): 2835-2838.
Cefali, E. A., P. D. Simmons, et al. (2007). "Aspirin reduces cutaneous flushing after administration of an optimized extended-release niacin formulation." *Int J Clin Pharmacol Ther* 45(2): 78-88.
Cooper, A., N. O'Flynn, et al. (2008). "Risk assessment and lipid modification for primary and secondary prevention of cardiovascular disease: summary of NICE guidance." *BMJ* 336(7655): 1246-1248.

(Continued)

*Primary Examiner* — Gina C Justice
(74) *Attorney, Agent, or Firm* — Choate, Hall & Stewart LLP; Andrea L. C. Reid; Kevin M. Henry

(57) ABSTRACT

The present invention relates to compounds, and compositions, useful for treating dyslipidemia.

15 Claims, 18 Drawing Sheets

(56) References Cited

OTHER PUBLICATIONS

Dishy, V., F. Liu, et al. (2009). "Effects of Aspirin When Added to the Prostaglandin D2 Receptor Antagonist Laropiprant on Niacin-Induced Flushing Symptoms." *J Clin Pharmacol* 49(4): 416-422.

Duggal, J. K., M. Singh, et al. (2010). "Effect of Niacin Therapy on Cardiovascular Outcomes in Patients With Coronary Artery Disease." *Journal of Cardiovascular Pharmacology and Therapeutics* 15(2): 158-166.

Fleischman, A., S. E. Shoelson, et al. (2008). "Salsalate Improves Glycemia and Inflammatory Parameters in Obese Young Adults." *Diabetes Care* 31(2): 289-294.

Goldberg, A., P. Alagona, et al. (2000). "Multiple-dose efficacy and safety of an extended-release form of niacin in the management of hyperlipidemia." *The American journal of cardiology* 85(9): 1100-1105.

Goldberg, R. B. and T. A. Jacobson (2008). "Effects of Niacin on Glucose Control in Patients With Dyslipidemia." *Mayo Clinic Proceedings* 83(4): 470-478.

Goldfine, A. B., V. Fonseca, et al. (2010). "The Effects of Salsalate on Glycemic Control in Patients With Type 2 Diabetes." *Annals of Internal Medicine* 152(6): 346-357.

Goldfine, A. B., R. Silver, et al. (2008). "Use of Salsalate to Target Inflammation in the Treatment of Insulin Resistance and Type 2 Diabetes." *Clinical and Translational Science* 1(1):36-43.

Gordon, D., J. Probstfield, et al. (1989). "High-density lipoprotein cholesterol and cardiovascular disease. Four prospective American studies." *Circulation* 79(1): 8-15.

Grundy, S. M., G. L. Vega, et al. (2002). "Efficacy, Safety, and Tolerability of Once-Daily Niacin for the Treatment of Dyslipidemia Associated With Type 2 Diabetes: Results of the Assessment of Diabetes Control and Evaluation of the Efficacy of Niaspan Trial." *Arch Intern Med* 162(14): 1568-1576.

Guyton, J., R. and P. Simmons, D. (2009). "Flushing and other dermatologic adverse events associated with extended-release niacin therapy." *Journal of Clinical Lipidology* 3(2): 101-108.

Jackevicius, C. A., M. Mamdani, et al. (2002). "Adherence With Statin Therapy in Elderly Patients With and Without Acute Coronary Syndromes." *JAMA: The Journal of the American Medical Association* 288(4): 462-467.

Jacobson, T. A. (2010). "A Hot Topic in Dyslipidemia Management—How to Beat a Flush": Optimizing Niacin Tolerability to Promote Long-term Treatment Adherence and Coronary Disease Prevention. *Mayo Clinic Proceedings* 85(4): 365-379.

Kashyap, M., L. , M. McGovern, E., et al. (2002). "Long-term safety and efficacy of a once-daily niacin/lovastatin formulation for patients with dyslipidemia* * A complete list of participants in the Research Group and Publication Committee appears in the Appendix." *The American journal of cardiology* 89(6): 672-678.

Kastelein, J. J. P., S. I. van Leuven, et al. (2007). "Effect of Torcetrapib on Carotid Atherosclerosis in Familial Hypercholesterolemia." *N Engl J Med* 356(16): 1620-1630.

Knopp, R. H., P. Alagona, et al. (1998). "Equivalent efficacy of a time-release form of niacin (Niaspan) given once-a-night versus plain niacin in the management of hyperlipidemia." *Metabolism* 47(9): 1097-1104.

Knopp, R. H., B. M. Retzlaff, et al. (2009). "The SLIM Study: Slo-Niacin® and Atorvastatin Treatment of Lipoproteins and Inflammatory Markers in Combined Hyperlipidemia." *Journal of Clinical Lipidology* 3(3): 167-178.

Knopp, R. H., J. Ginsberg, et al. (1985). "Contrasting effects of unmodified and time-release forms of niacin on lipoproteins in hyperlipidemic subjects: Clues to mechanism of action of niacin." *Metabolism* 34(7): 642-650.

Kush, D., D. Y. Hu, et al. (2009). "Flushing Profile of Extended-Release Niacin/Laropiprant at Initiation of Therapy in Asian Lipid Clinic Patients." *Cardiology* 114(3): 192-198.

Lai, E., I. De Lepeleire, et al. (2007). "Suppression of Niacin-induced Vasodilation with an Antagonist to Prostaglandin D2 Receptor Subtype 1." *Clin Pharmacol Ther* 81(6): 849-857.

Maccubbin, D., H. E. Bays, et al. (2008). "Lipid-modifying efficacy and tolerability of extended-release niacin/laropiprant in patients with primary hypercholesterolaemia or mixed dyslipidaemia." *International Journal of Clinical Practice* 62(12): 1959-1970.

McKenney, J. (2004). "New Perspectives on the Use of Niacin in the Treatment of Lipid Disorders." *Arch Intern Med* 164(7): 697-705.

McKenney, J., H. Bays, et al. (2008). "Safety Profile of Extended-Release Niacin/Laropiprant in Patients With Dyslipidemia." *Atherosclerosis Supplements* 9(1): 194-195.

McKenney, J., M. , P. Jones, H., et al. (2007). "Comparative effects on lipid levels of combination therapy with a statin and extended-release niacin or ezetimibe versus a statin alone (the COMPELL study)." *Atherosclerosis* 192(2): 432-437.

McKenney, J. M., J. D. Proctor, et al. (1994). "A Comparison of the Efficacy and Toxic Effects of Sustained- vs Immediate-Release Niacin in Hypercholesterolemic Patients." *JAMA: The Journal of the American Medical Association* 271(9): 672-677.

McQuaid, K., R. and L. Laine (2006). "Systematic Review and Meta-analysis of Adverse Events of Low-dose Aspirin and Clopidogrel in Randomized Controlled Trials." *The American journal of medicine* 119(8): 624-638.

Natarajan, P., K. K. Ray, et al. (2010). "High-Density Lipoprotein and Coronary Heart Disease: Current and Future Therapies." *J Am Coll Cardiol* 55(13): 1283-1299.

Nicholls, S. J., E. M. Tuzcu, et al. (2008). "Cholesteryl Ester Transfer Protein Inhibition, High-Density Lipoprotein Raising, and Progression of Coronary Atherosclerosis: Insights From Illustrate (Investigation of Lipid Level Management Using Coronary Ultrasound to Assess Reduction of Atherosclerosis by CETP Inhibition and HDL Elevation)." *Circulation* 118(24):2506-2514.

Oberwittler, H. and M. Baccara-Dinet (2006). "Clinical evidence for use of acetyl salicylic acid in control of flushing related to nicotinic acid treatment." *International Journal of Clinical Practice* 60(6): 707-715.

Parhofer, K. G. (2009). "Review of extended-release niacin/laropiprant fixed combination in the treatment of mixed dyslipidemia and primary hypercholesterolemia." *Vascular Health and Risk Management* 5: 901-908.

Patrono, C., C. Baigent, et al. (2008). "Antiplatelet Drugs*." *Chest* 133(6 suppl): 199S-233S.

Shah, S., R. Ceska, et al. (2010). "Efficacy and safety of extended-release niacin/laropiprant plus statin vs. doubling the dose of statin in patients with primary hypercholesterolaemia or mixed dyslipidaemia." *International Journal of Clinical Practice* 64(6): 727-738.

Taylor, A. J., L. E. Sullenberger, et al. (2004). "Arterial Biology for the Investigation of the Treatment Effects of Reducing Cholesterol (ARBITER) 2: A Double-Blind, Placebo-Controlled Study of Extended-Release Niacin on Atherosclerosis Progression in Secondary Prevention Patients Treated With Statins." *Circulation* 110(23): 3512-3517.

Taylor, A. J., T. C. Villines, et al. (2009). "Extended-Release Niacin or Ezetimibe and Carotid Intima-Media Thickness." *N Engl J Med* 361(22): 2113-2122.

Thakkar, R. B., M. L. Kashyap, et al. (2009). "Acetylsalicylic Acid Reduces Niacin Extended-Release-Induced Flushing in Patients with Dyslipidemia." *American Journal of Cardiovascular Drugs* 9: 69-79.

The Coronary Drug Project Research Group (1975). "Clofibrate and Niacin in Coronary Heart Disease." *JAMA: The Journal of the American Medical Association* 231(4): 360-381.

The Search Collaborative Group (2008). "SLCO1B1 Variants and Statin-Induced Myopathy—A Genomewide Study." *N Engl J Med* 359(8): 789-799.

Whitney, E. J., R. A. Krasuski, et al. (2005). "A Randomized Trial of a Strategy for Increasing High-Density Lipoprotein Cholesterol Levels: Effects on Progression of Coronary Heart Disease and Clinical Events." *Annals of Internal Medicine* 142(2): 95-104.

Wolfe, M., L. , S. Vartanian, F. , et al. (2001). "Safety and effectiveness of Niaspan when added sequentially to a statin for treatment of dyslipidemia." *The American journal of cardiology* 87(4): 476-479.

(56) References Cited

OTHER PUBLICATIONS

National Institutes of Health (2002). "Third Report of the National Cholesterol Education Program (NCEP) Expert Panel on Detection, Evaluation, and Treatment of High Blood Cholesterol in Adults (Adult Treatment Panel III) Final Report." NIH Publication No. 02-5215.

Lamon-Fava, Stefania, Diffenderfer, Margaret R., et al. (2008). "Extended0Release Niacin Alters the Metabolism of Plasma Apolipoprotein (Apo) A-I and ApoB-Containing Lipoproteins." *Journal of the American Heart Association* 28: 1672-1678.

Vittone, Francesca, Chait, Alan et al. (2007). "Niacin plus Simvastatin Reduces Coronary Stenosis Progression Among Patients with Metabolic Syndrome Despite a Modest Increase in Insulin Resistance: A Subgroup Analysis of the HDL-Atherosclerosis Treatment Study (HATS)." *J Clin Lipidol.* 1(3): 203-210.

Gilmer, J. F., Moriarity, L.M. et al. (2002). "Isosorbide-based aspirin prodrugs. II. Hydrolysis kinetics of isosorbide diaspirinate." *Eur J Pharm Sci.* 16(4-5): 297-304.

Moriarty, L. M., Lally, M. N. et al. (2008). "Discovery of a "true" aspirin prodrug." *J Med Chem* 51(24): 7991-9.

Cefali, E. A., Simmons, P. D. et al. (2006). "Improved control of niacin-induced flushing using an optimized once-daily, extended-release niacin formulation." *Int J Clin Pharacol Ther.* 44(12): 633-40.

Souza Lima, M. A. (1985). "Ulcers of the small bowel associated with stomach-bypassing salicylates." *Arch Intern Med.* 145(6): 1139.

Knopp, R. H. (2000). "Evaluating niacin in its various forms." *Am J Cardiol.* 86(12A): 51L-56L.

Guyton, J. R., Goldberg, A. C. et al. (1998). "Effectiveness of once-nightly dosing of extended-release niacin alone and im combination for hypercholesterolemia." *Am J Cardiol.* 82(6): 737-43.

International Search Report for PCT/IB2011/002285, 4 pages (mailed Feb. 9, 2012).

Written Opinion for PCT/IB2011/002285, 6 pages (mailed Feb. 9, 2012).

\* cited by examiner

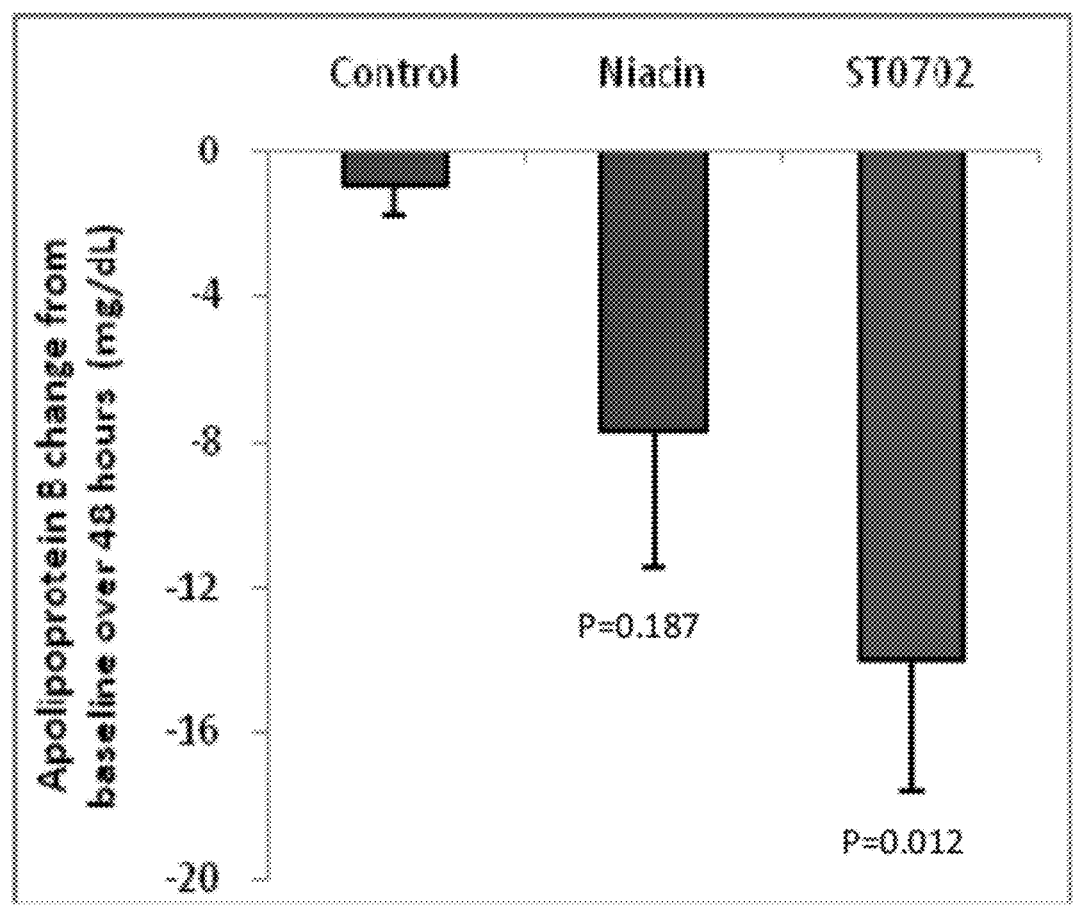

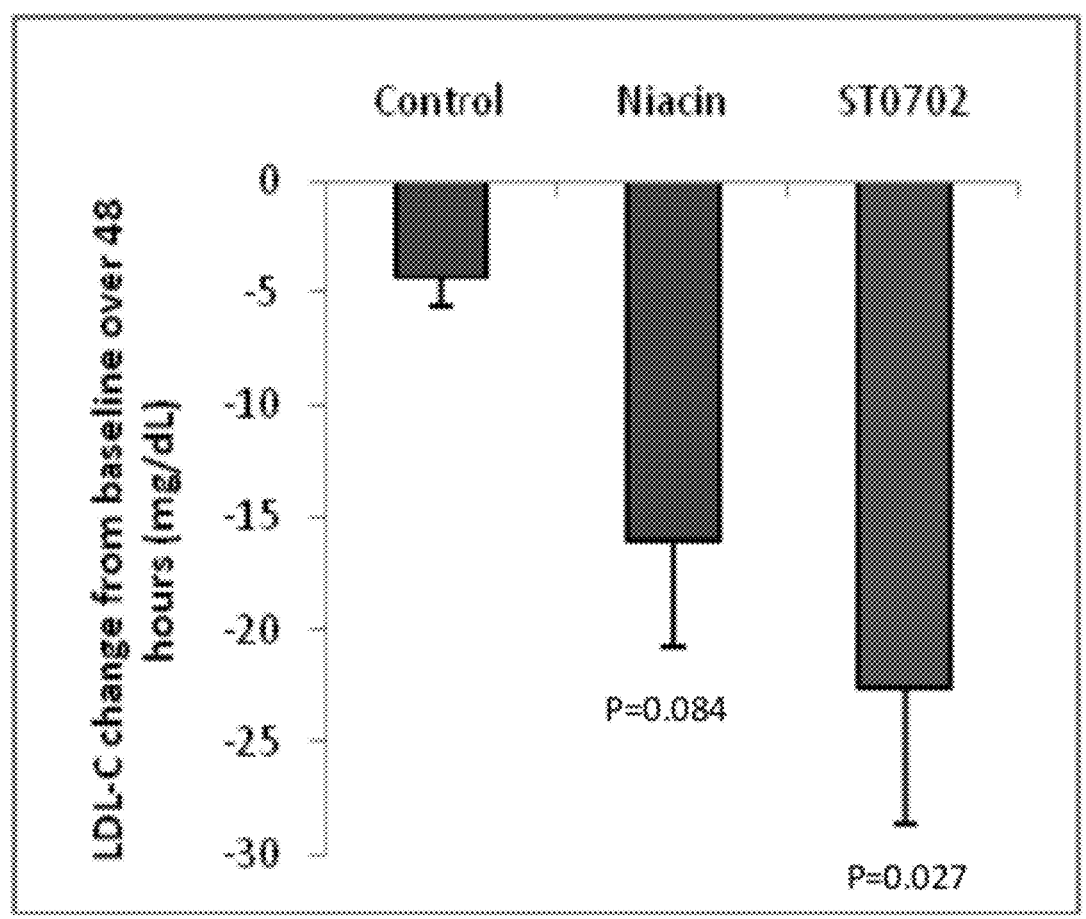

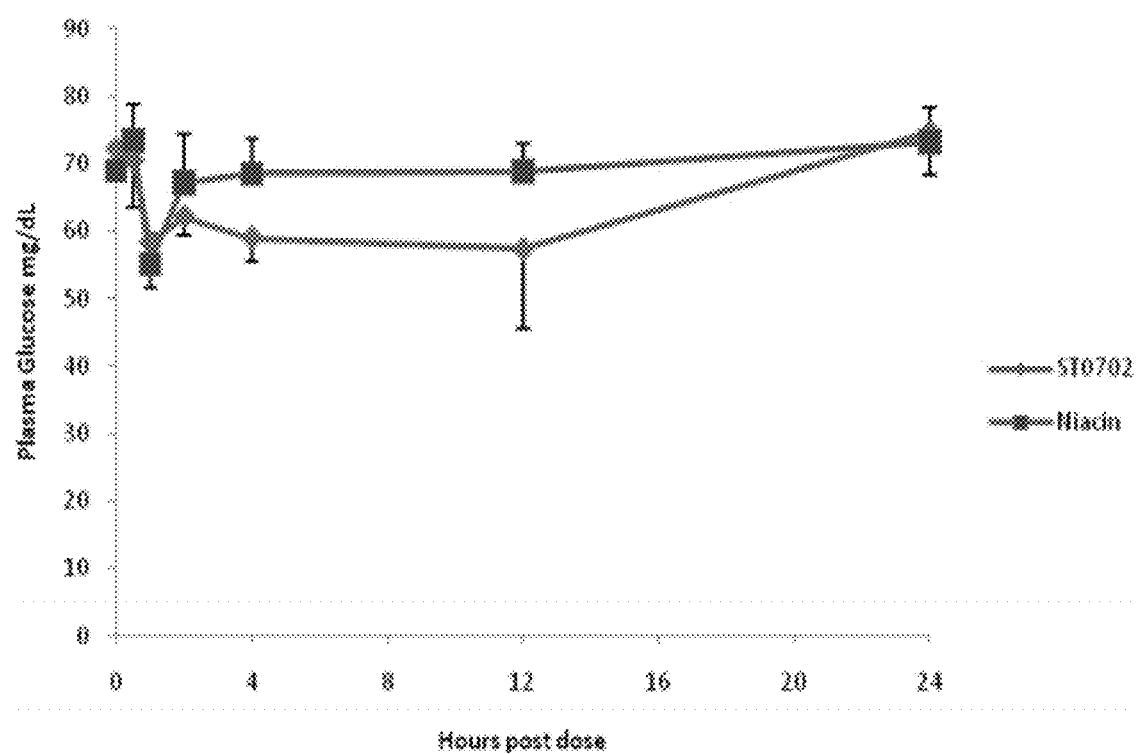

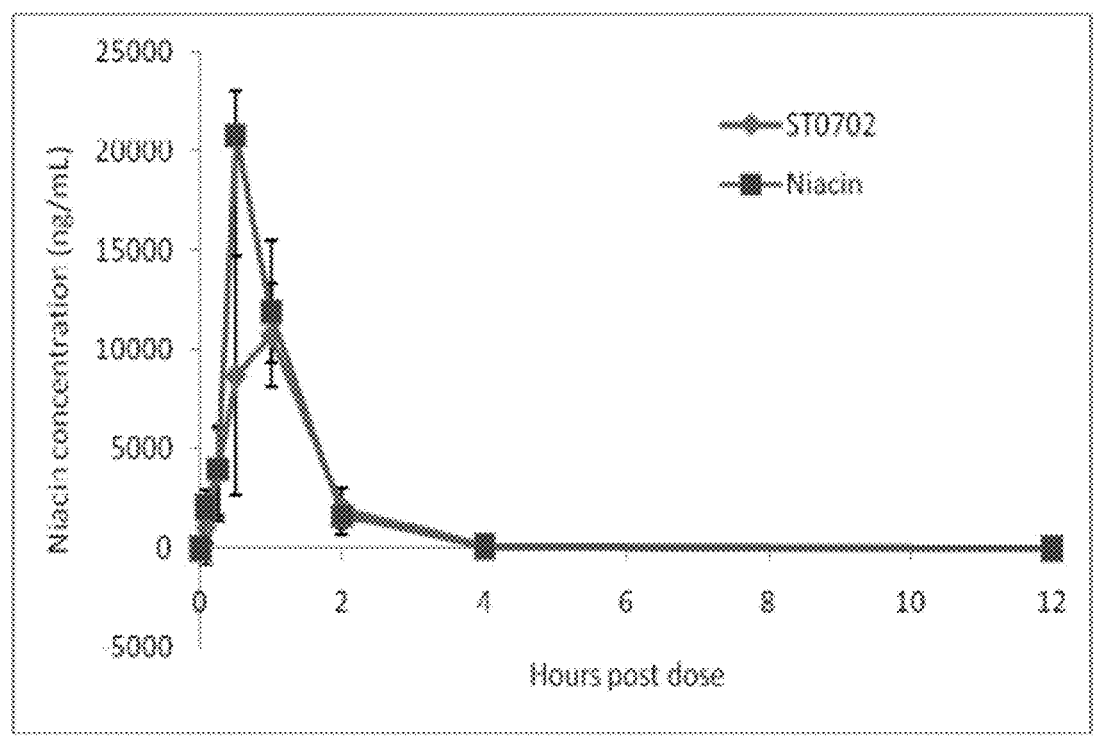

TREATMENT FOR DYSLIPIDEMIA

CROSS-REFERENCE TO RELATED APPLICATIONS

The present application claims priority to U.S. Provisional Application No. 61/361,337, filed Jul. 2, 2010, which is herewith incorporated by reference in its entirety.

BACKGROUND

Dyslipidemia is a disruption in the amount of lipids in the blood. Dyslipidemia may be defined as any one of or a combination of (but not limited to) elevated low density lipoprotein cholesterol (LDL), elevated apolipoprotein B, elevated triglycerides (TGs), elevated lipoprotein(a), elevated apolipoprotein A, reduced high density lipoprotein cholesterol (HDL) or reduced apolipoprotein A1. Abnormal cholesterol and TG levels have been implicated in the onset of atherosclerosis, coronary artery disease, stroke and heart attacks. According to the NHANES III database 35% of men and 13% of women have low blood serum HDL cholesterol levels (defined as less than 40 mg/L). Various studies have shown that individuals with low HDL levels have a higher incidence of cardiovascular (CV) events than those with HDL levels greater than 65 mg/L. In the Framingham Heart Study, just under half (44%) of coronary events were observed in persons with HDL levels less than 40 mg/L (Castelli 1986). While cholesterol and TG levels can be mediated by lifestyle changes, some patients do not realize a significant enough reduction in overall cholesterol levels. To that effect, many patients supplement lifestyle changes with pharmaceutical agents to regulate cholesterol and TG levels.

Reduction of LDL cholesterol is currently the primary goal of dyslipidemia management. Along with clinically significant LDL cholesterol reductions, HMG CoA Reductase inhibitor (statin) therapy has morbidity and mortality benefit proven in more than 175,000 patient years of randomized data (Baigent. 2005).

The global antidyslipidemic market was worth $26.6 billion in 2007. The US accounted for 55% ($18.8 billion) with Japan, France, Germany, Italy, Spain and the UK together accounting for 23% of the market share. As expected, the market is dominated by statins which accounted for 61% of the US market share in 2007. The market shrank in 2007 following Zocor's loss of patent protection in the US. Further falls in revenue are expected in 2010 when the first generic versions of atorvastatin become available. The US dyslipidemic market is predicted to be worth $11.4 billion in 2017. However, this fall in revenue will predominantly impact the statin sub-section of the market. Sales of cholesterol uptake inhibitors e.g. ezetimibe, nicotinic acid and other dyslipidemic agents, such as probucol and benfluorex, accounted for almost $2.5 billion in sales in 2007 (which represented a 19% growth that year) and accounted for 13% of the US dyslipidemic sales. The compound annual growth rate (CAGR) for this class of drugs between 2004 and 2007 was 26% compared with −9% for statin therapy.

Approximately 1 in 2 statin treated patients in clinical practice do not reach their designated LDL goal. Furthermore, at least 1 in 10 patients in practice stop taking statin therapy because of side-effects (Avorn, Monette et al. 1998; Benner, Glynn et al. 2002; Jackevicius, Mamdani et al. 2002).

While statin therapy has been shown to be clinically effective in managing elevated LDL, it is less effective on reduced HDL, reduced apolipoprotein A1, elevated lipoprotein(a), elevated apolipoprotein A and elevated TGs. In the context of increases in the population prevalence of metabolic syndrome, particularly linked to non-LDL cholesterol dyslipidemia, there is considerable interest in optimizing dyslipidemia therapy using companion or add-on therapy. With intensifying competition in the market place and statin patent expires, there remains a need to develop novel therapies for the treatment of dyslipidemia and associated diseases.

DETAILED DESCRIPTION OF THE DRAWINGS

FIG. 1 depicts a progress curve for the disappearance of isosorbide-2-aspirinate-5-nicotinate (ST0702) following incubation (in vitro) in 50% human plasma diluted with pH 7.4 buffer at 37° C. ST0702 undergoes rapid conversion to a series of hydrolysis products as a result of the actions of butyrylcholinesterase (BuChE) in plasma. The products are aspirin, isosorbide-2-salicylate-5-nicotinate (salicylate), salicylic acid (a hydrolysis product of the salicylate) leading to formation of isorobide-5-nicotinate and eventually nicotinic acid.

Figure 5:
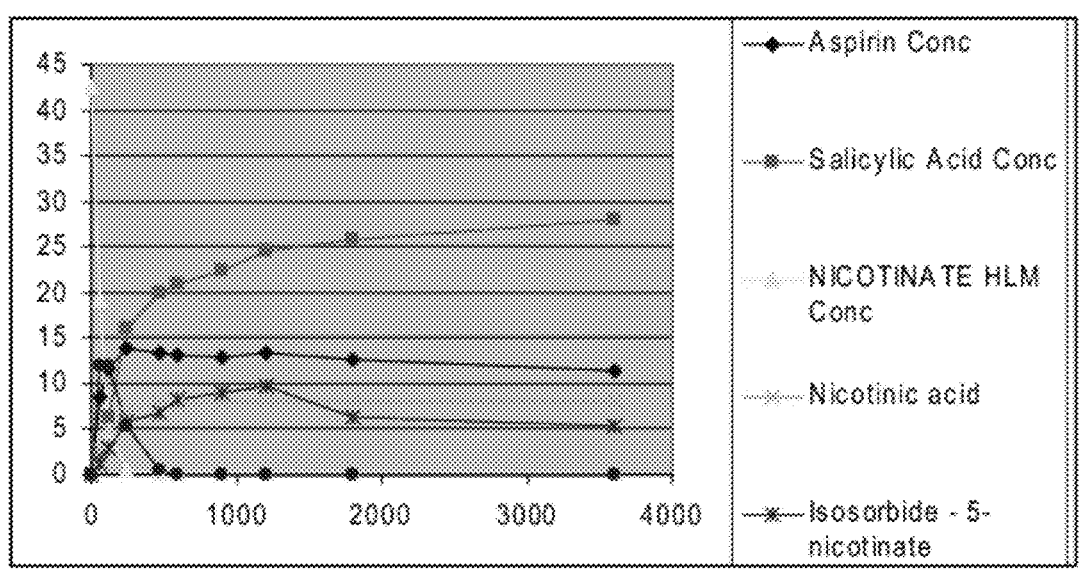
Figure 6:
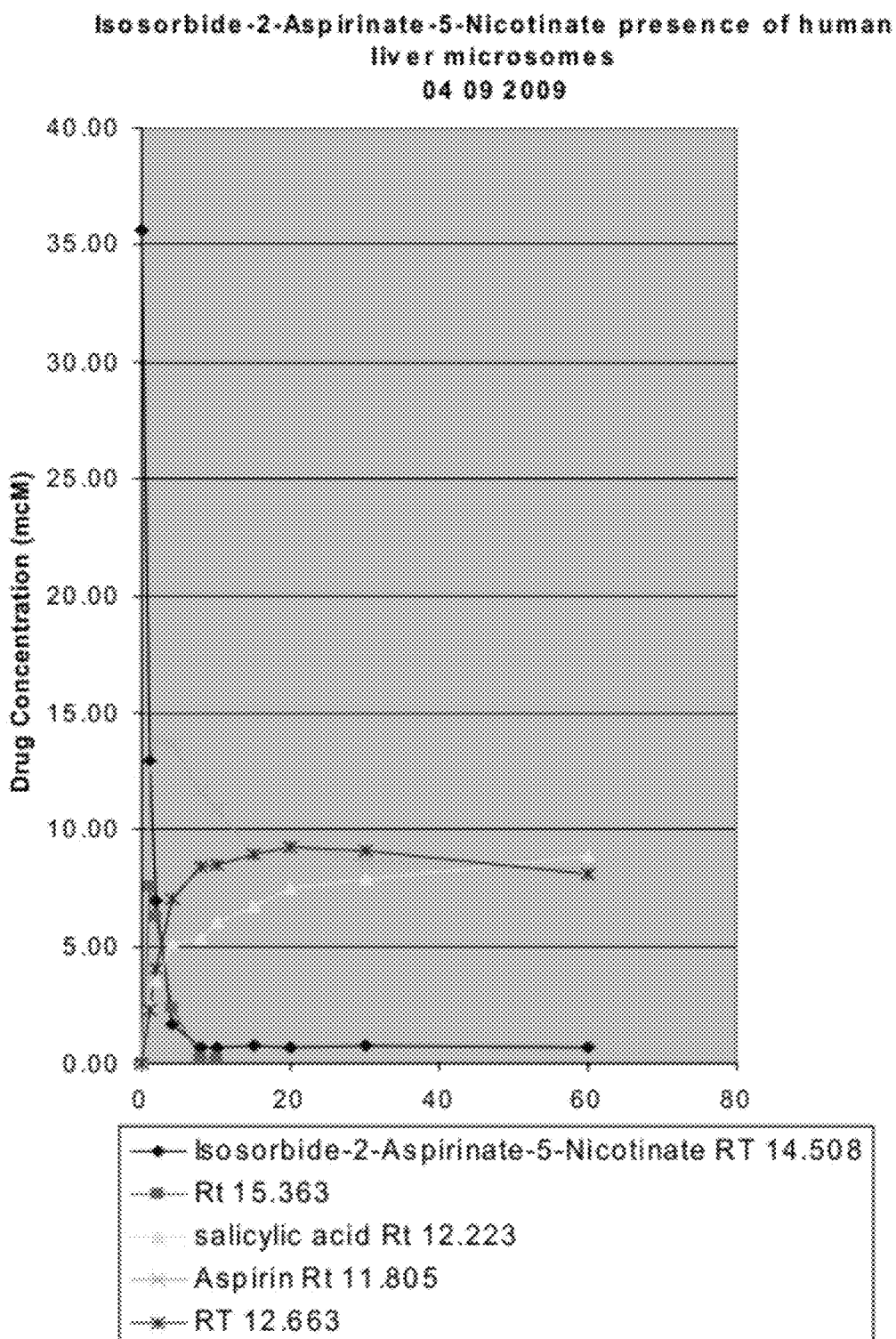

FIGS. 5 and 6 depict graphs demonstrating the incubation of ST0702 in the presence of human liver microsomes. Microsomes from human hepatocytes (post mortem tissue) were diluted with pH 7.4 buffer and the suspension warmed to 37° C. ST0702 was introduced and samples withdrawn at successive time intervals. The products include aspirin, isosorbide-2-salicylate-nicotinate, nicotinic acid and isosorbide-5-nicotinate. Hepatocytes contain carboxylesterase (CE)-1 and CE-2 in addition to BuChE and there is evidence of more significant direct hydrolysis at position 5 leading to direct nicotinic acid production.

Figure 7:
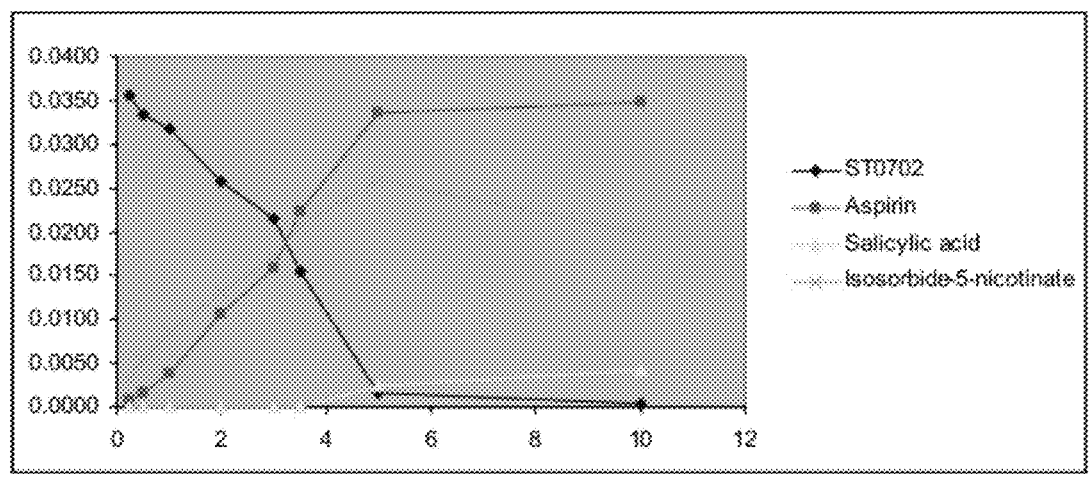

FIG. 7 depicts a progress curve following incubation of ST0702 in the presence of microsomes from the human intestinal wall. These contain most CE-2 which causes hydrolysis predominantly at the isosorbide-2-position liberating aspirin and isosorbide-5-nicotinate.

Figure 8:
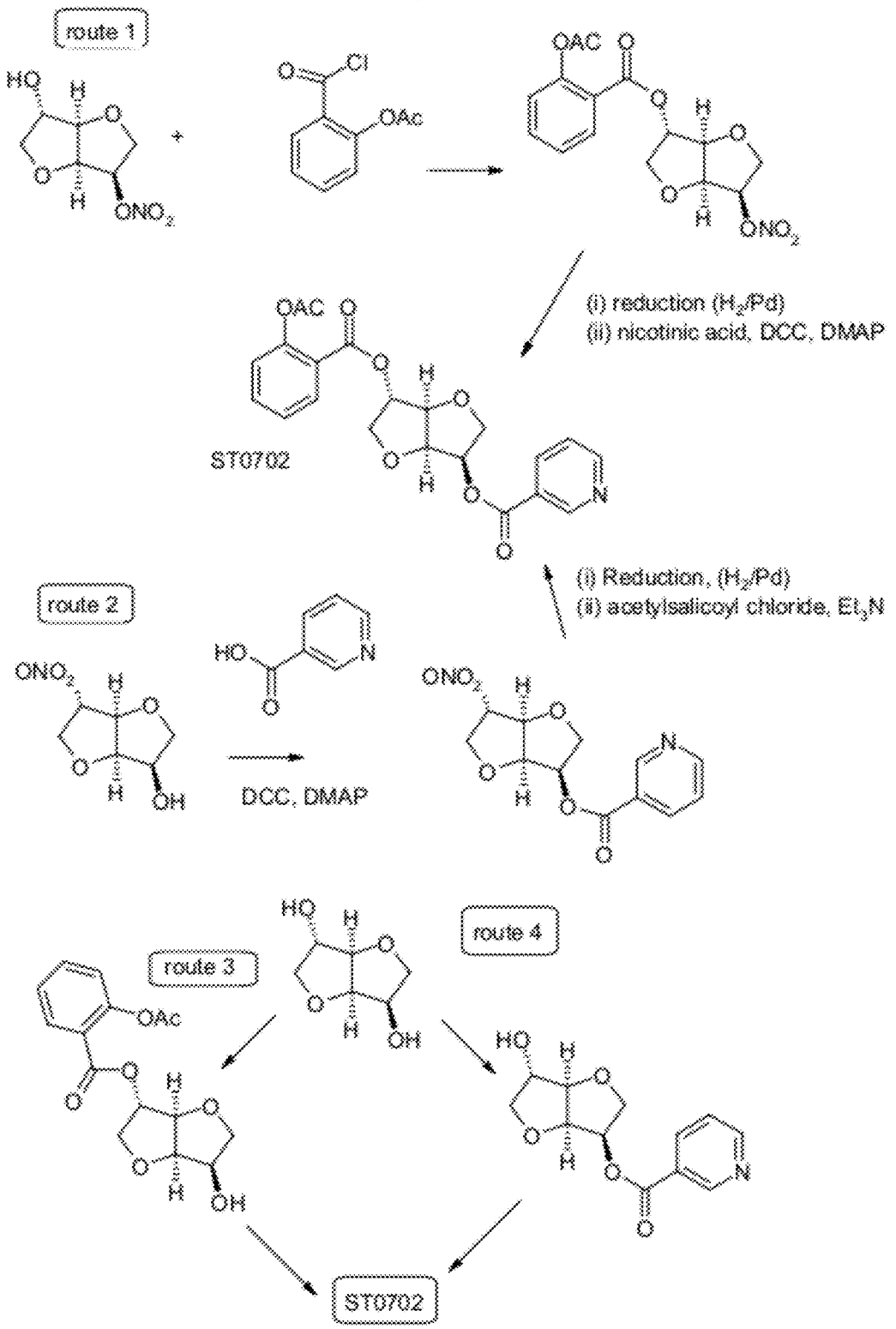

FIG. 8 depicts the chemical synthesis of ST0702.

FIG. 9 depicts the impact of nicotinic acid (niacin) and ST0702 on serum apolipoprotein B (FIG. 9A) and LDL-C (FIG. 9B) levels in a prospective, randomized, cross-over, non-human primate study of ST0702 versus equimolar amounts of nicotinic acid, n=6 per group. Data shown represent the mean and SEM of change values from baseline to 48 hours (both fasting). P values shown are versus control (paired sample T-Test).

FIG. 10 depicts the impact of test articles on serum glucose levels over 24 hours in a prospective, randomized, cross-over, non-human primate study of ST0702 versus equimolar amounts of nicotinic acid (niacin), n=6 per group. Data shown represent the mean and SEM of change values from baseline to 24 hours (both fasting). The 4 hour timepoint represents a significant reduction in plasma glucose in the ST0702 group (p=0.02) but not the niacin group (p=0.94).

Figure 11A:
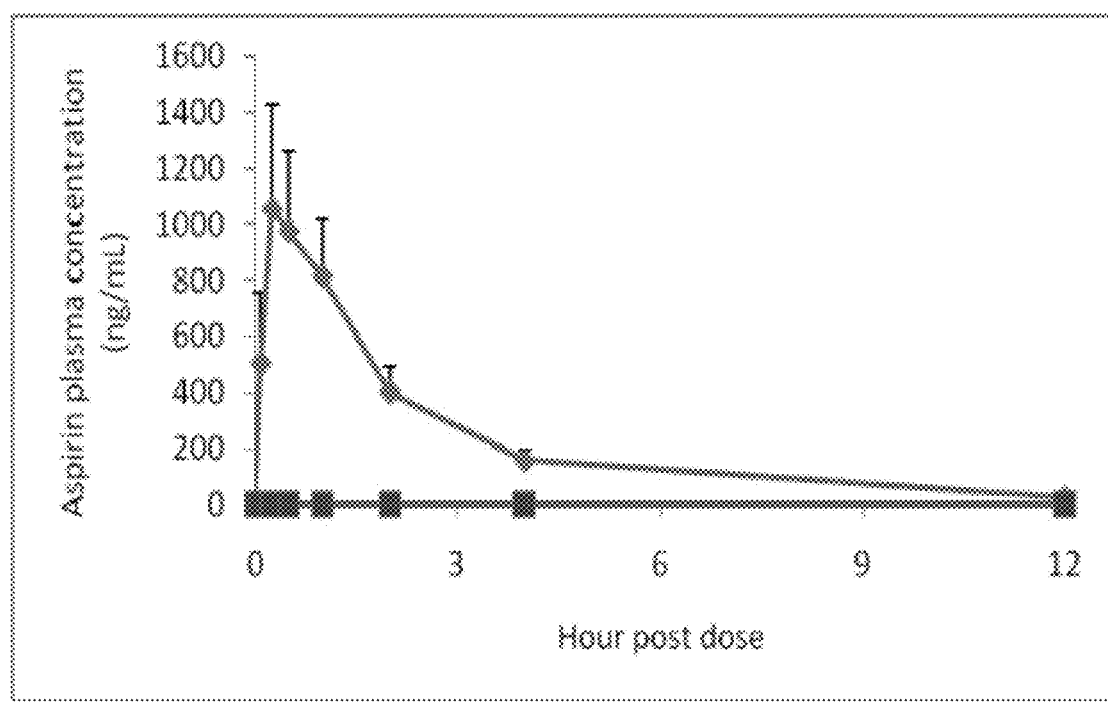
Figure 11C:
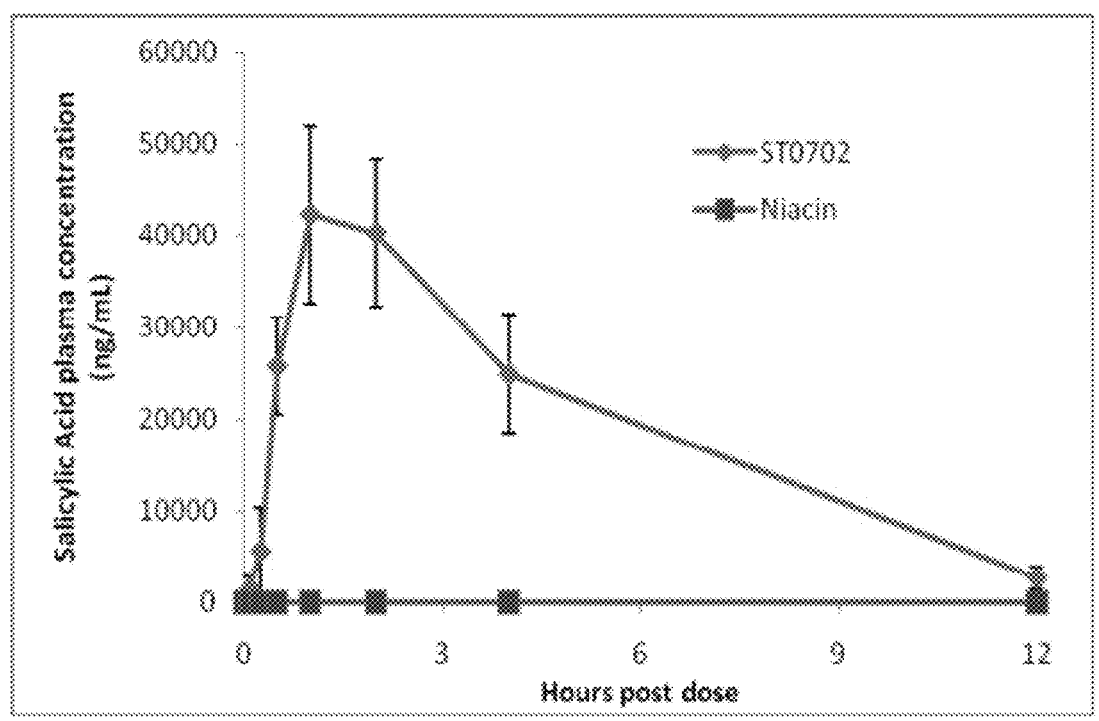

FIG. 11 depicts the ST0702 comparative pharmacokinetic profiles of aspirin (FIG. 11A), nicotinic acid (niacin) (FIG. 11B) and salicylic acid (FIG. 11C) in a prospective, randomized, cross-over, non-human primate study of ST0702 versus equimolar amounts of nicotinic acid (niacin), n=6 per group following single daily dose at time 0. Because of the short half-lives of aspirin and nicotinic acid (niacin), data are shown over the first 12 hours for illustrative purposes. Data represent the mean and SEM of values.

Figure 12:
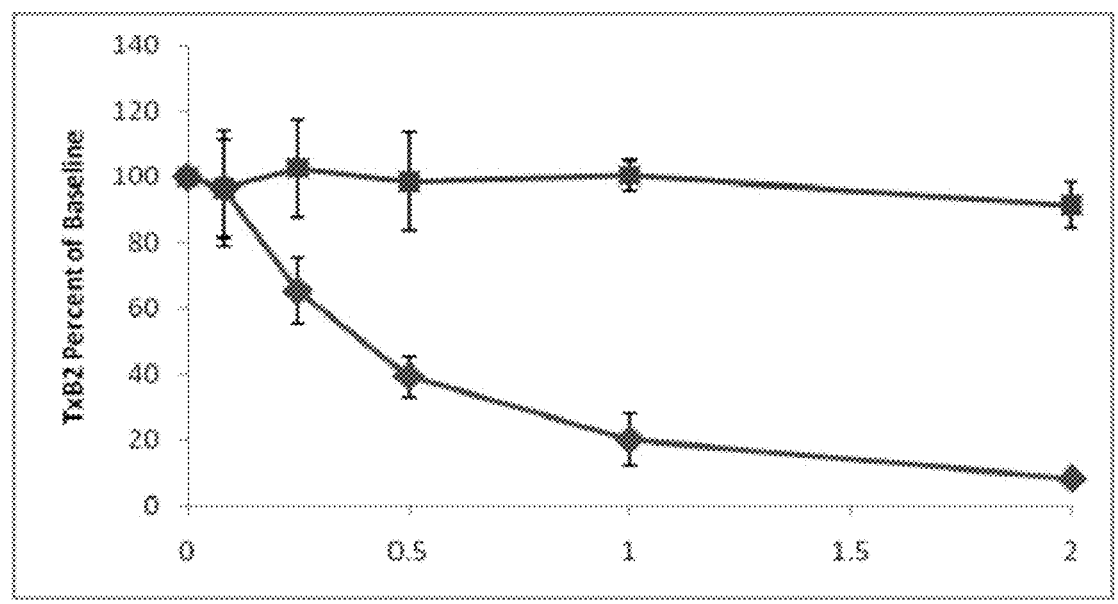

FIG. 12 depicts the serum thromboxane B2 (TxB2) profiles of nicotinic acid (niacin) and ST0702 groups over 2 hours post dosing in a prospective, randomized, cross-over, non-human primate study of ST0702 versus equimolar amounts of nicotinic acid (niacin), n=6 per group following single daily dose at time 0. Data represent the mean and SEM of values. All values from 15 minutes onwards were significantly reduced within the ST0702 group (all p<0.01) and between nicotinic acid (niacin) and ST0702 groups (all p<0.01) and sustained at 24 and 48 hours.

Figure 13:
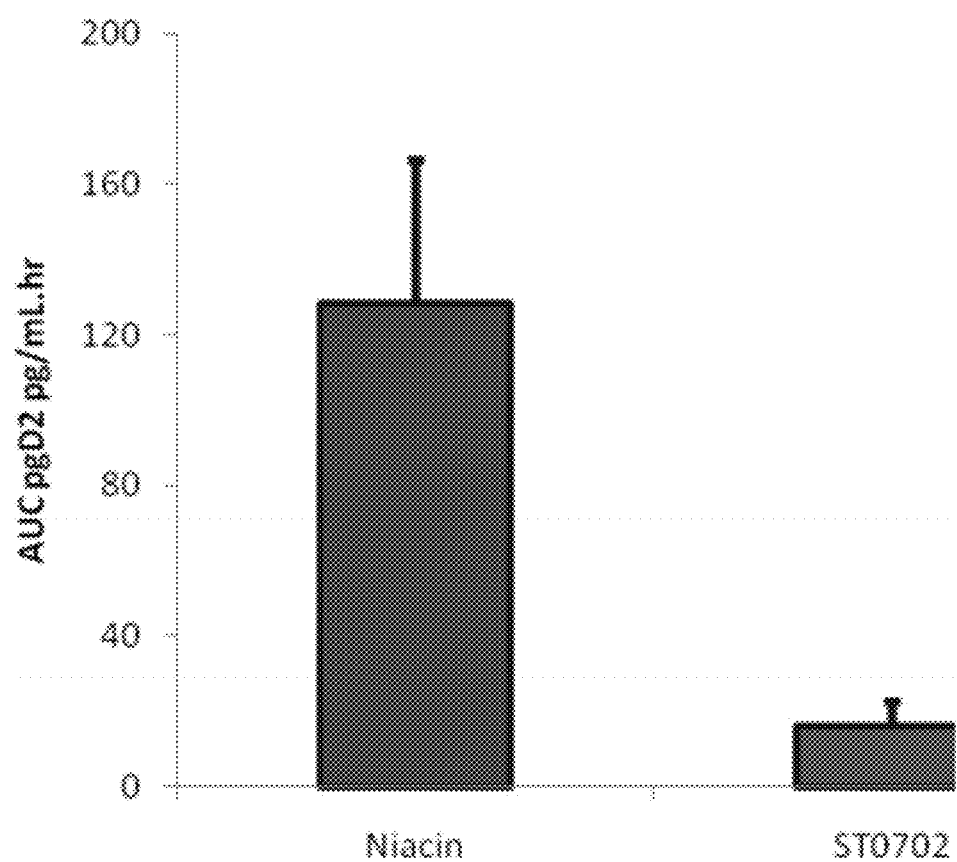

FIG. 13 depicts area under the curve (AUC) values for prostaglandin D2 (PGD2) profiles of nicotinic acid (niacin) and ST0702 groups over 24 hours post dosing in a prospective, randomized, cross-over, non-human primate study of ST0702 versus equimolar amounts of nicotinic acid (niacin), n=6 per group following single daily dose at time 0. Data represent the mean and SEM of values.

Figure 14:
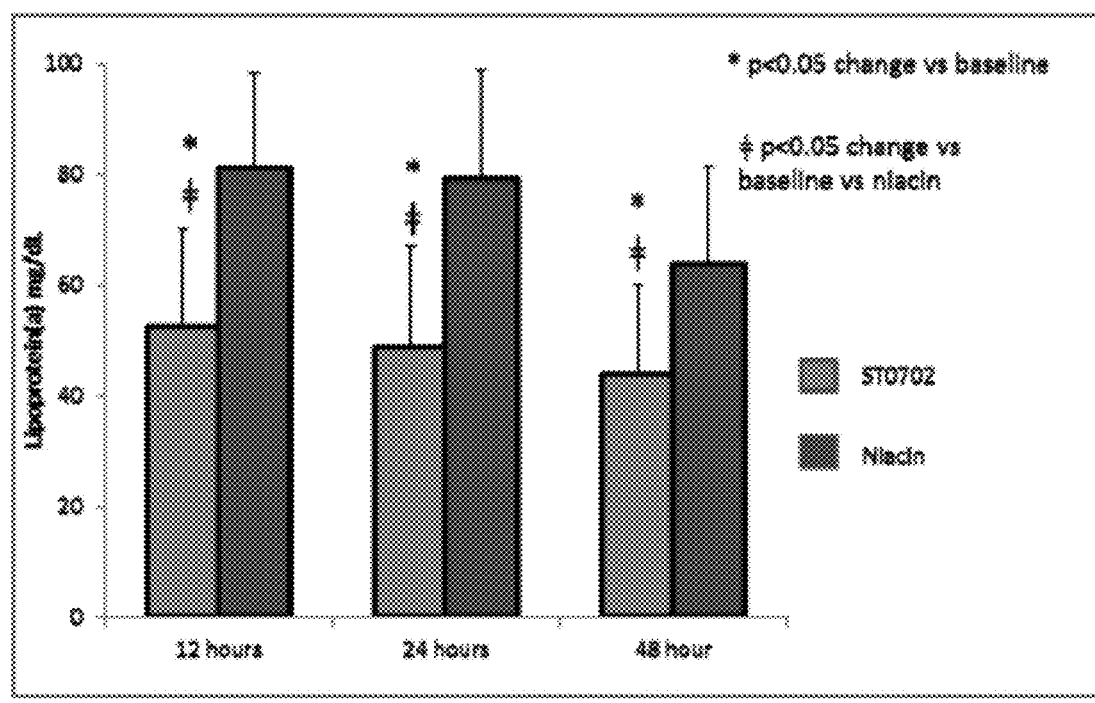

FIG. 14 depicts lipoprotein(a) levels at 12, 24 and 48 hours in a parallel group, subset analysis with of the ST0702 versus equimolar niacin (28 mg/kg niacin equivalents), n=3 per group following single daily doses at time 0 and 24 hours.

Figure 15:
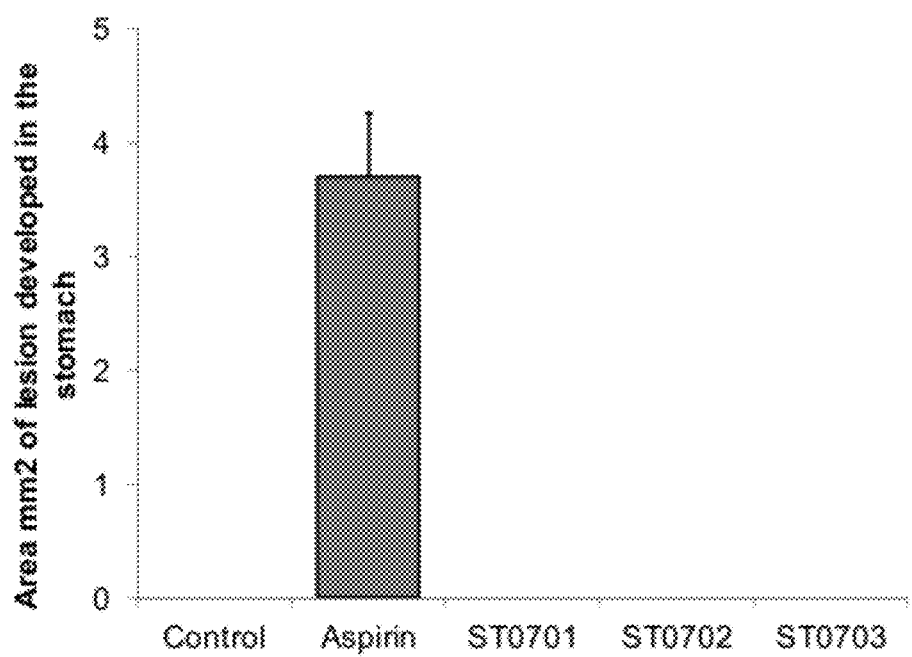

FIG. 15 depicts the impact of high doses of aspirin and aspirin prodrugs (including ST0702) using daily aspirin doses of 30 mg/Kg or molar equivalents over 3 days in rabbits.

DETAILED DESCRIPTION OF CERTAIN EMBODIMENTS OF THE INVENTION

Nicotinic acid is also known as niacin. However, the term nicotinic acid is preferred as some published sources use the term "niacin" to refer interchangeably to nicotinic acid and/or nicotinamide (vitamin B3). Whereas nicotinic acid and nicotinamide are identical in their functions as vitamins (nicotinic acid is converted into nicotinamide via Nicotinamide Adenosine Diphosphate where it prevents a dietary deficiency called pellagra or "rough skin"), they differ in their pharmacological actions. Nicotinic acid (unlike nicotinamide), is a vasodilator and was the first lipid modifying therapy shown to reduce the risk of myocardial infarction and long-term mortality by 27% and 11% respectively (The Coronary Drug Project Research Group 1975; Canner, Berge et al. 1986). Nicotinic acid favorably modifies the entire lipid panel in patients with dyslipidemia (Guyton, Goldberg et al. 1998; Knopp, Davidson et al. 1998; Lamon-Fava, Diffenderfer et al. 2008) by reducing LDL cholesterol and its apolipoprotein B component, raising HDL cholesterol and its apolipoprotein AI component, reducing lipoprotein (a) and its apolipoprotein A component and lowering TGs. Thus, nicotinic acid improves cholesterol profiles by substantially increasing HLD and reducing TG levels while providing modest reductions in LDL cholesterol It is the only lipid lowering drug that reduced Lipoprotein (a) (Lp(a)) levels.

In adipose tissue, nicotinic acid reduces lipolysis of TG by lipase. In the liver, it reduces TG synthesis thereby reducing hepatic very low density lipoprotein (VLDL) production and LDL levels. It also promotes lipoprotein lipase activity, increasing clearance of chylomicrons from dietary fat and cholesterol. Finally, it increases HDL levels by decreasing the fractional clearance of apoA-I and augmenting reverse cholesterol transport. Following oral dosing, crystalline nicotinic acid (>1 g) is almost completely absorbed, achieves peak plasma concentrations 30-60 minutes later and has a half life of about 60 minutes.

While the outcome of studies designed to evaluate the hypothesis that HDL raising therapy with nicotinic acid in high doses is of benefit in the setting of very low LDL levels are awaited, nicotinic acid remains indicated in statin intolerant patients in the secondary prevention of cardiovascular disease. Furthermore, as described above, 40-50% of patients studies do not achieve low LDL cholesterol levels in clinical practice and the relative benefit over ezetimibe on carotid-intima medial thickness (CIMT) shown in the ARBITER-6 study suggests that nicotinic acid is an important option as combination therapy with statins.

Epidemiological studies suggest that a 1 mg/L increase in HDL is associated with a 2% to 4% reduction in adverse coronary heart disease (CHD) outcomes (Gordon et al 1989). Currently, nicotinic acid is the most effective available pharmacologic means to raise HDL cholesterol levels, with increases of 15% to 35% (Expert panel on detection, evaluation and treatment of high blood cholesterol in adults, 2002). In addition to its potent activity on HDL, nicotinic acid significantly reduces LDL cholesterol, TG and Lp(a) levels. Nicotinic acid's effects on the various lipids are compared with other pharmacologic interventions in Table 1. It follows a relatively flat dose response curve so most of the rise in HDL with nicotinic acid occurs at daily doses of 1 g to 1.5 g (Knopp 2000, Capuzzi 2000). The effect of nicotinic acid on LDL cholesterol is dose dependent (Wolfe 2001).

TABLE 1

Drugs for the treatment of adult dyslipidemias.

| Drug Class | LDL cholesterol | HDL cholesterol | TG |
| --- | --- | --- | --- |
| Statins | −18 to −55% | +5 to 15% | −7 to −30% |
| Bile acid sequestrants | −15 to −30% | +3 to +5% | No change or increase |
| Fibrates | −5 to −20% | +10 to +20% | −20 to −50% |
| Ezetimibe | −18 to −24% | +3% | No change |
| NICOTINIC ACID | −5 to −25% | +15 to +35% | −20 to −50% |

Although its mechanism of action is incompletely understood, central to its efficacy appears to be interaction with a G1-protein-coupled transmembrane receptor (GPR109A) in adipose tissue resulting in reduced free fatty acid release. However, its use in clinical practice is limited by poor adherence and persistence arising in particular from prostaglandin D2 (PGD2) release from epidermal Langerhans cells causing flushing at prostaglandin DP1 receptors in the vasculature and gastro-intestinal toxicity. Thus, while nicotinic acid remains the most effective method by which to raise HDL levels, various side-effects associated with the administration of a therapeutically effective amount of nicotinic acid have impeded the development and adoption of such therapy, as detailed below.

Nicotinic Acid as Monotherapy

The Coronary Drug Project (CDP) evaluated the effect of immediate-release (IR) nicotinic acid monotherapy on 8,431 men with a history of myocardial infarction (MI) during the period 1966 and 1975 (Coronary Drug Research Project Research Group, 1975). Over a five year follow up period, the incidence of non-fatal re-infarction was reduced by 27%. Moreover, after a mean follow-up of 15 years, nicotinic acid contributed to a significant decrease in all-cause mortality by 11% (p<0.001) (Canner, Berge et al. 1986). However, there was a significant drop-out and lower adherence in the nicotinic acid arm because of side-effects related to this formulation.

In an evaluation of 131 patients with hyperlipidemia randomized to the extended release (ER) nicotinic acid (Niaspan®), ER nicotinic acid was initiated at a dose of 375 mg/day, and increased in 500 mg increments at 4 week intervals to a maximum of 3,000 mg/day. The effect on HDL started to appear at the 500 mg/day dose and peaked at the 2,500 mg/day dose, with a 30% increase in HDL from baseline. TG levels started to decrease at the 1,000 mg dose reaching maximal reduction of 44% at the 3,000 mg/day dose. Significant decreases in LDL cholesterol became apparent with the 500 mg/day dose reaching 21% at the 3,000 mg/day dose (Goldberg 2000).

Nicotinic Acid in Combination Therapies
1. Nicotinic Acid in Combination with Statins Given the superior efficacies of nicotinic acid and statins on HDL and LDL cholesterol, respectively, combining them provides a regimen with greater overall lipid-altering efficacy than either drug can provide alone. In one study, the addition of 1 g/day of nicotinic acid to a stable dose of statin monotherapy lowered LDL levels an additional 8% and raised HDL levels an additional 24%, whereas the addition of 2 g/day of nicotinic acid lowered LDL an additional 20% and raised HDL cholesterol levels an additional 27% (Wolfe 2001).

The safety and effectiveness of a once daily single tablet combination of nicotinic acid (2 g) and lovastatin (40 mg) was also evaluated in 814 patients. LDL and TG were reduced by 45% and 42% respectively and HDL was increased 41% (Kashyap, 2002).

The SLIM Study (Slo-Niacin® and Atorvastatin Treatment of Lipoproteins and Inflammatory Markers in Combined Hyperlipidemia), published in 2009, evaluated the effects of Slo-Niacin® and atorvastatin given separately and together, to determine efficacy on the combined abnormalities of TG, LDL and HDL. A total of 42 men and women with LDL >130 mg/L and HDL <45 mg/L (men) or <55 mg/L (women) were randomized to 3 months of atorvastatin 10 mg/day or incremental doses of Slo-Niacin® to 1500 mg/day. The alternate drug was added in the next 3-month segment (Knopp 2009). The effects of each intervention on lipid profile is summarized in Table 2.

TABLE 2

Effect of Slo-Nicotinic Acid ® and Lipitor ® on lipid profile in the SLIM study.

| Drug therapy | TG | LDL | HDL |
|---|---|---|---|
| Slo-Niacin ® | −15% | −12% | +8% |
| Atorvastatin | −26% | −36% | +6% |
| Combination | −33% | −43% | +10% |

The HDL-Atherosclerosis Treatment Study (HATS) evaluated ER nicotinic acid (Slo-Niacin®) plus simvastatin combination therapy in patients with low HDL and normal LDL cholesterol levels. After a treatment period of three years, compared with a mean 3.9% progression in coronary stenosis with placebo, nicotinic acid/simvastatin therapy caused a mean regression of 0.4% (p<0.001) and had an increase in HDL levels of 26%. In addition, the treatment with simvastatin and nicotinic acid resulted in a 60-90% relative reduction in major clinical events (defined by death from coronary causes, non-fatal MI, stroke or revascularization) vs. placebo (p=0.02). (Brown et al., 2001). Interestingly, in a later subgroup analysis, the powerful effect on progression of coronary stenosis seen in the overall study was not evident in the patients with dysglycaemia. (Vittone, F, Chait, A, Morse, B, Fish, J, Brown, G, Zhao, X, J Clin Lipidol. 2007 July; 1(3): 203-210)

The COMPELL study compared four treatment arms in 293 patients with dyslipidemia. It was shown that rosuvastatin (40 mg daily), simvastatin/ezetimibe (40 mg/10 mg daily), rosuvastatin with nicotinic acid (20 mg/2 g daily) and atorvastatin with nicotinic acid (40 mg/2 g daily) resulted in identical reductions of LDL cholesterol (−50% to −55%). Therapies without nicotinic acid resulted in an increase in HDL of approximately 5%-10% while the increases in combination therapy using nicotinic acid was 22%-25%. In addition, combination therapy using nicotinic acid reduced TG by 40-50% (McKenney 2007).

Data from the Arterial Biology for the Investigation of the Treatment Effects of Reducing Cholesterol (ARBITER-2) study also showed that the addition of ER nicotinic acid to statin therapy could slow the progression of atherosclerosis, as measured by carotid intima-media thickness (CIMT) among coronary heart disease patients with low HDL cholesterol levels. Once daily nicotinic acid 1,000 mg was added to background simvastatin therapy in 167 patients with known coronary artery disease and low levels of HDL (<45 mg/L). HDL increased by 21% (from 39 to 47 mg/L) in the nicotinic acid group. After 12 months the CIMT increased significantly in the placebo group but was unchanged in the nicotinic acid group (Taylor et al 2004).

The follow-up study, ARBITER 6 was designed to compare HDL lowering therapy with ER nicotinic acid vs. LDL lowering therapy with ezetimibe on atherosclerosis progression in patients already receiving statin therapy. The trial was stopped early in 2009 when it was observed that patients receiving nicotinic acid had a significant reduction in CIMT at both 8 and 14 months (Taylor 2009).

The Atherothrombosis Intervention in Metabolic Syndrome with Low HDL-C/High Triglyceride and Impact on Global Health Outcomes (AIM-HIGH) study was designed to test the hypothesis that treatment with Niaspan® plus simvastatin would provide superior CV outcomes to simvastatin given alone in a population of >3,000 patients with vascular disease and atherogenic dyslipidemia. However, this study was stopped prematurely on the basis of futility. In the absence of further details at this time, it appears that the study was underpowered. The neutral result also raises, on one hand, a number of now well established concerns about the value of HDL modification in the setting of very low LDL-C values and on the other hand concerns about potential adverse effects of ER/sustained release versions of niacin on glycaemia, hepatotoxicity and gastric toxicity in a predominantly diabetic/prediabetic population (see below adverse effects of niacin). The AFREGS trial evaluated combinations of lipid-lowering therapy in the treatment of patients with coronary atherosclerosis and low HDL. In this study 143 patients were randomized to a combination of immediate release (IR) nicotinic acid, colestipol and gemfibrozil or placebo and followed for 30 months. There was a slight reduction in the primary composite CV endpoint in those treated with combination therapy (p=0.04) along with a small but statistically significant regression in coronary lesions. However, the study was probably underpowered to detect these differences (Whitney 2005).

In a meta-analysis of seven trials of secondary prevention, nicotinic acid was associated with a significant reduction in coronary artery revascularization (p=0.001), non-fatal MI (p<0.001), stroke and transient ischemic heart attack (TIA) (p=0.012). Compared with the placebo group nicotinic acid did not, however, show any advantage in reducing CV mortality (Duggal 2010).

In addition the Treatment of High Density Lipoprotein to Reduce the Incidence of Vascular Events (HPS-THRIVE) trial is currently underway to evaluate the efficacy of a combination tablet of nicotinic acid plus a prostaglandin analogue (lapopiprant) in reducing vascular end points. Approximately 25,000 patients will be evaluated, including more than 7,000 diabetic patients.

Adverse Events Associated with Nicotinic Acid

Despite convincing data on lipids and clinical events, nicotinic acid use in clinical practice is limited because of two main adverse effects: flushing and dyspepsia. These adverse effects are dose-dependent and are also associated with pruritus, rash, nausea, dyspepsia, abdominal pain and diarrhea. For example, treatment with nicotinic acid among all patients treated for dyslipidemia is less than 6% in the US, 3% in Canada and 2% in Europe (Shah 2010). Even among patients treated with nicotinic acid, doses are often suboptimal (<2 g/day) (Shah 2010). A further adverse effect which may be of concern in the management of patients with cardio-metabolic disorders and may comprise a large proportion of at-risk patients is the disturbance of glucose metabolism, or glycemic disturbance, associated with nicotinic acid. Disturbances of glucose metabolism in these patients may be associated with increased CVr risk. Furthermore, the current approaches to managing flushing as described below involve combinations of delayed/ER nicotinic acid and conventional aspirin which are less effective in improving HDL profile and can cause increased liver abnormalities (McKenney, Proctor et al. JAMA 1994)

1. Flushing 10-50% of patients in IR nicotinic acid trials discontinued therapy as a result of cutaneous flushing (McKenney 2004) which occurs in almost all individuals at the start of therapy. The long-acting (LA) formulation was developed to prevent this problem but was associated with increased hepatotoxicity. ER nicotinic acid (Niaspan®) produces significantly less flushing than IR nicotinic acid without increasing hepatoxic effects (Knopp, 1998). However, flushing is still a problem with this formulation. The summary of product characteristics for Niaspan® states that flushing episodes were reported by 88% of patients in clinical trials; 6% of patients discontinued treatment as a result.

Data from four multicenter randomized controlled trials (RCT) were pooled in an analysis by Guyton. Among 333 patients treated with ER nicotinic acid for three to six months, 83% reported at least one flushing episode compared with 18% in the placebo treated group. 76% rated flushing events as mild to moderate in intensity and 5% withdrew due to flushing. In an 8 week comparison with IR nicotinic acid at equivalent daily doses, the total number of flushing events was 76% lower in the ER group (Guyton 2009). A recent review stated that in clinical trials most (>60%) users experienced mild or moderate flushing which tended to reduce in frequency and severity with continued nicotinic acid treatment, even with advancing doses. Approximately 5-20% of all patients discontinue treatment because of flushing (Jacobson 2010).

Several approaches to niacin induced flushing have been developed. Delayed or modified release formulations of niacin can reduce but not abrogate niacin induced flushing at the expense of efficacy compared with IR formulations, where penetration of the drug into adipose may be reduced (Knopp, Ginsberg et al. 1985; McKenney, Proctor et al. 1994). Recently, a formulation of niacin with laropiprant, a specific prostaglandin DP1 receptor blocker, has been marketed in Europe but not the US where FDA concerns about the drug risk/benefit ratio arose. While up to one third of niacin users take cyclooxygenase 1 (COX1) inhibiting drugs such as aspirin or ibuprofen to blunt or prevent niacin induced flushing, it is known that higher doses are more effective with consequent dose dependent aggravation of gastro-intestinal (GI) side-effects from aspirin and the combination of aspirin and niacin 2. Gastrointestinal Irritation Approximately 20% of patients receiving IR nicotinic acid experience symptoms of GI irritation. Usually these symptoms are transitory and can be minimized by taking IR nicotinic acid with or after food. GI irritation and toxicity appears to also be a significant problem with ER nicotinic acid and product information for Niaspan® reports the occurrence of diarrhea, nausea, vomiting, abdominal pain and dyspepsia as common.

The exact etiology of GI toxicity associated with nicotinic acid is unknown. However, it may be due to topical effects on the gut mucosa and it is also well established that immediate release nicotinic acid has better GI tolerability; there was an 8% vs 38% incidence of nausea with IR versus SR niacin (Knopp, Ginsberg et al. Metabolism 1985) and in a separate study a 39% vs 56% incidence of GI disturbances with IR versus SR niacin respectively (McKenney, Proctor et al. JAMA 1994).

Taken together, we believe that conventional approaches to managing nicotinic acid flushing aggravate GI toxicity on three levels: [1] aspirin topical GI toxicity [2] aspirin and nicotinic acid mediated topical GI toxicity and [3] increased nicotinic acid GI toxicity associated with ER and/or SR nicotinic acid formulations. If this is holds true, it may explain the low levels of compliance and usage of this potentially life saving therapy.

3. Glycemic Disturbance

Hyperglycemia is an important CV risk factor and yet is another important side-effect associated with nicotinic acid therapy. In most clinical trials, mean changes in fasting blood glucose levels were generally modest and transient, possibly due to adjustments in therapy (McKenney 2004). Nicotinic acid-induced hyperglycemia is more prevalent in patients with diabetes, 10% to 35% of whom it is estimated will require a change in hypoglycemic therapy. In addition, a few patients with impaired fasting glucose levels (but not diabetics) may develop diabetes, requiring initiation of hypoglycemic therapy. The prevalence of these effects seems to be similar with IR and ER nicotinic acid, although percent increases seem to be higher with IR nicotinic acid.

In a study of diabetic patients, 16 weeks of therapy with 1,500 mg/day nicotinic acid induced only minor changes of fasting glucose and HbAlc. However, during the course of the study oral anti-diabetic medication and insulin dose was adjusted (Grundy 2002). In a recent study, higher doses of nicotinic acid resulted in a slight worsening of glycemic control (p=0.048) in the ADVENT (Assessment of Diabetes Control and Evaluation of the Efficacy of Niaspan® Trial) trial of type 2 diabetic patients randomly assigned to nicotinic acid or placebo. When given at doses <2.5 g, nicotinic acid was associated with a 4% to 5% increase in fingerstick glucose levels. However, nicotinic acid may or may not have effect on HbAlc, which may be transient only during up titration of doses (Goldberg 2008).

In summary, glycemic disturbance has been well described in the use of nicotinic acid. Although the predominant concern has been in patients with diabetes, a large group of patients in a "pre-diabetic" state is emerging in western populations due to lifestyle and diet factors. Data collected on a group of 177 consecutive, consenting patients screened for cardiovascular risk factors (age 54.5+/−13.3 years, 45.8% male, 39% with established CVD or diabetes) demonstrates a prevalence of diabetes in only 3.7% of the population. However more than 6 times this number, or 23.7%, had impaired fasting glucose using American Diabetic Association criteria (>5.5 mmol/L) indicating the presence of such a "pre-diabetic" state.

Furthermore, of the total 177 patients, 26% had elevated HDL using European Society of Cardiology (2007) criteria. A total of 63.3% had dyslipidemia and could benefit from nicotinic acid therapy. However, of the subset with elevated HDL, approximately 28% had both elevated HDL and impaired fasting glucose. Of the subset with dyslipidemia, 71% also had impaired fasting glucose. Therefore, the argument that glycemic disturbance associated with nicotinic acid is only relevant in a small proportion of users does not hold true in this analysis. In a majority of patients who indicated nicotinic acid therapy, the resulting glycemic disturbance may cause adverse CV effects and deterioration of glucose control, putting patients in a diabetic state and/or resulting in augmentation of hypoglycemic therapy, thereby exposing patients to additional side-effects of medication.

Furthermore, while dysglycaemia is a feature of all currently available high dose niacin products, it is also known that IR nicotinic acid has better glycaemic tolerability than SR versions; there was an non-significant 0.8 mmol/L vs a significant 2.1 mmol/L increase in dysglycaemia with IR versus SR niacin (McKenney, Proctor et al. JAMA 1994).

Aspirin

Aspirin is the most widely used drug worldwide for the prevention of CVD. Approximately 36% of the US adult population (more than 50 million people) take aspirin regularly for CVD prevention, translating into roughly 10 to 20 billion aspirin tablets annually (Campbell, Smyth et al. 2007). Aspirin has been thoroughly evaluated as an anti-platelet drug and was found to prevent vascular death by approximately 15% and non-fatal vascular events by about 30% in a meta-analysis of over 100 randomized trials in high risk patients (secondary prevention) (Antithrombotic Trialists Collaboration, 2002). However, individual trial data show substantial heterogeneity, ranging from no statistically significant benefits in patients with peripheral vascular disease to approximately 50% risk reduction in patients with unstable angina. In terms of absolute benefit, these protective effects of aspirin translate into avoidance of a major vascular event in 50 per 1,000 patients with unstable angina treated for 6 months and in 36 per 1,000 patients with prior MI, stroke, or TIA treated for approximately 30 months (Antithrombotic trialists collaboration, 2002). Trials of aspirin in primary prevention have shown 25%-33% reductions in risk of MI.

The optimal dose of aspirin which maximizes efficacy and minimizes toxicity continues to be debated. Placebo-controlled trials have used dosages ranging from 50 mg/day to 1,300 mg/day (Antithrombotic trialists collaboration, 2002). Other clinical trials have evaluated dosages as low as 30 mg/day and as high as 1,500 mg/day (Campbell 2007). In the US, the FDA recommends dosages ranging from 50 mg/day to 1,300 mg/day for CVD prevention (Campbell 2007). In the US, 81 mg/day of aspirin is prescribed most commonly (>60%), followed by 325 mg/day (35%) (Campbell 2007). Evidence suggests that dosages greater than 75 mg to 81 mg do not enhance efficacy, whereas larger doses are associated with an increased incidence of bleeding events, primarily related to GI toxicity (Campbell 2007). The Antithrombotic Trialists Collaboration review found no difference in efficacy between low-dose (<150 mg) and medium dose (150 mg-325 mg) aspirin (Antithrombotic Trialists Collaboration, 2002).

The lowest effective dosages for the various indications of aspirin are shown in Table 3. The American College of Chest Physicians state in their most recent guidelines "the saturability of the antiplatelet effect of aspirin at low doses, the lack of dose response relationship in clinical studies evaluating its antithrombotic effects, and the dose dependence of its side-effects all support the use of as low a dose of aspirin as has been found to be effective in the treatment of various thromboembolic disorders". (These doses are summarized in Table 3). Use of the lowest effective dose of aspirin (50 to 100 mg/day for long-term treatment) is currently the most appropriate strategy to maximize its efficacy and minimize its toxicity" (CHEST 2008).

TABLE 3

Vascular disorders for which aspirin has been shown to be effective and lowest effective dose (CHEST 2008).

| Disorder | Lowest effective daily dose |
| --- | --- |
| TIA and ischaemic stroke | 50 mg* |
| Men at high CV risk | 75 mg |
| Hypertension | 75 mg |
| Stable angina | 75 mg |
| Unstable angina | 75 mg* |
| Severe carotid artery stenosis | 75 mg* |
| Polycythemia | 100 mg |
| Acute MI | 160 mg |
| Acute ischaemic stroke | 160 mg* |

*Higher doses have been tested in other trials and were not found to confer any greater risk reduction.

However, there are potentially adverse CV effects associated with the use of higher doses of aspirin. Concern has been raised by potentially adverse impact of COX-2 inhibition on longer term CV risk, which resulted in the withdrawal in 2004 of rofecoxcib, or VIOXX®, from the marketplace. The concern associated with elevated CV risks of COX-2 inhibition has extended to other Non Steroidal Anti-Inflammatory Drugs (NSAIDs), many of which are COX-2 inhibiting agents. At higher doses (>1.0 to 1.3 g/day), aspirin also shows COX-2 inhibitory action. It has been suggested that the beneficial effects of aspirin on platelet inhibition are lost when higher doses of aspirin are used, possibly due to COX-2 inhibition at higher doses.

Moreover, aspirin is indicated as a first line anti-platelet agent in secondary prevention of cardiovascular disease in 70 out of our 177 consecutive community adult population. Of these 70 patients, 33% had reduced HDL. A total of 64.3% had dyslipidemia. Therefore, our data demonstrate that up to 2 out of 3 patients with established cardiovascular disease and require aspirin may benefit from nicotinic acid therapy.

1. Aspirin Reduces Nicotinic Acid Flushing

An additional advantage of the combined use of aspirin and nicotinic acid is the reduction of nicotinic acid flushing.

Current steps which are advised in the management of nicotinic acid flushing is as follows:

Initiate therapy using small divided doses and slowly titrate upwards over several weeks.

Take aspirin or other NSAID 20 minutes prior to the morning dose to reduce prostaglandin mediated vasodilatation (see below).

Avoid taking nicotinic acid with alcohol, spicy foods, or hot beverages.

Avoid interrupting therapy; continuous therapy promotes tolerance.

Use ER instead of IR nicotinic acid and take at bedtime.

Aspirin and other NSAIDs have been found to have some efficacy suppressing nicotinic acid-induced flushing by preventing the production of prostaglandins. Findings from studies specifically evaluating adjunctive or prophylactic aspirin or NSAIDs to attenuate nicotinic acid flushing were summarized by Jacobson (Jacobson 2010). The main findings are listed below.

- 325 mg aspirin significantly (p<0.001 vs. placebo) attenuated flushing symptoms when administered 30-60 minutes, but not 15 or 120 minutes, before IR nicotinic acid. An aspirin dose of 650 mg was not superior to 325 mg.
- Pre-treatment with 325 mg of aspirin 30 minutes before nicotinic acid was significantly superior to 200 mg ibuprofen.
- 325 mg aspirin was superior to 80 mg of aspirin in mitigating flushing with 0.5 g IR nicotinic acid.

Jacobsen reported that the flushing-specific discontinuation rate in a four week study was 1.8% among patients randomized to receive 325 mg aspirin before ER nicotinic acid compared with 9.4% who did not receive aspirin (p=0.007). 15% of patients receiving aspirin experienced moderate or greater flushing during the first week of treatment vs. 29% not receiving aspirin (p=0.01). Pre-treatment with aspirin significantly reduced mean maximal flushing severity, number of moderate or greater flushing episodes and the incidence of flushing by 18% (p=0.014) (Thakkar 2009). However, despite the success of aspirin in ameliorating these side-effects, the mean rate of treatment discontinuation because of nicotinic acid flushing is approximately 6.5% even with adjunctive aspirin (Oberwittler 2006).

Two new initiatives to reduce nicotinic acid induced flushing have been reported. ER nicotinic acid was reformulated with a different coating to optimize its dissolution, absorption and metabolic profiles. This new formulation resulted in a reduced intensity and duration of flushing. The flushing comparison was based on the administration of a single dose of 2,000 mg/day of the reformulated nicotinic acid ER tablet and the commercial nicotinic acid ER tablet given to male volunteers without prior dose titration. 89% of subjects experienced flushing during treatment with the reformulated product, which was significantly less than with the commercial one (98%) (p=0.0027). Reformulated ER resulted in a 42% decrease in flush intensity (p=0.0001) and a 43% reduction in flush duration (p=0.001) relative the commercial nicotinic acid ER (Cefali 2006). This new formulation is currently licensed in the US.

Accordingly, use of moderate doses of aspirin (e.g. 325-650 mg daily) with nicotinic acid may give the best reduction in nicotinic acid flushing. However, these higher doses of aspirin are associated with GII toxicity.

Laropiprant

Nicotinic acid-induced flushing is mediated primarily by prostaglandin D2 ($PGD_2$), which stimulates $PGD_2$ receptor-1 (DP1) in the skin. Laropiprant, a potent, once daily, highly selective DP1 antagonist has been combined with ER nicotinic acid into a single tablet (Tredaptive®). In a single dose study, concomitant laropiprant significantly reduced flushing associated with 1.5 g ER nicotinic acid by 47%, 67% and 74% for a 30 mg, 100 mg and 300 mg dose of laropiprant respectively (Lai 2007). Recently it was shown that the rate of moderate/severe flushing can be reduced from 50% to 24% by adding laropiprant to nicotinic acid (Kush 2009). In a study involving 4,700 patients, the addition of laropiprant to ER nicotinic acid reduced the rate of discontinuation due to flushing from 16.6% to 7.2% and the overall discontinuation rate from 31.5% to 25.3% (McKenney 2008).

In another study, 10% of the ER nicotinic acid/laropiprant group discontinued treatment because of flushing compared with 22% of the ER nicotinic acid monotherapy group (p<0.001). During the initiation phase of this study (weeks 2-24), 14% of patients taking ER nicotinic acid/laropiprant experienced moderate or severe flushing ≥1 day per week as compared with 29% of those taking ER nicotinic acid (p<0.001) (Maccubin 2008).

Shah et al. demonstrated a significant improvement in lipid parameters by adding ER nicotinic acid/laropiprant to ongoing statin therapy vs. doubling of the statin dose. LDL cholesterol and TG were reduced by 10.0% and 17.6% respectively and HDL increased by 15.8% in the ER nicotinic acid/laropiprant group (n=572). These figures were 5.5%, 4.0% and 0.2% in the statin dose doubled group (n=595) (Shah 2010). The rate of discontinuation due to adverse events was higher in the ER nicotinic acid/laropiprant group (14.9%) than the statin double group (7.4%). Cutaneous reactions reported were flushing (11.1%), feeling hot (1.5%), paraesthesia (1.7%), pruritus (8.0%), rash (1.8%) and erythema (1.0%) (Shah 2010). In a phase 1 study, co-administration of 325 mg of aspirin did not confer significant incremental benefits in reducing the incidence and severity of residual flushing associated with laropiprant/nicotinic acid (Dishy 2009).

The manufactures of Tredaptive® state in the SPC that flushing occurs in 12.3% of patients taking the drug and the rates of discontinuation from clinical trials as a result of this adverse effect was 7.2% (vs 16.6% for ER nicotinic acid).

Other potential agents that might ameliorate nicotinic acid induced flushing include agents targeting the serotonergic component of the vasocutaneous reaction (e.g. cyproheptadine). Other candidates include flavonoids which inhibit mast cell $PGD_2$ secretion (Jacobson 2010).

However, in the US, the FDA has taken a view that laropiprant is a potentially toxic, new chemical which requires 5 more years of follow up data given the chronic, potentially lifelong nature of therapy in managing dyslipidemia.

Neither aspirin nor laropiprant completely relieves the flushing effect. Aspirin can increase the risk of GI events and/or bleeding. In a systematic review of 22 randomized trials of low dose aspirin (75-325 mg daily) the absolute annual increased risk of bleeding was 1.3 per 1000 patients for all major bleeding episodes (mostly GI) (McQuaid 2006). Doses as low as 10 mg can produce GI damage. More than 75% of patients will have at least occult bleeding with daily aspirin use even at low doses. Laropiprant also causes adverse GI effects. In an analysis of three studies, 16.5% of the ER nicotinic acid/laropiprant treated group experienced GI adverse events (vs. 11.7% in the ER nicotinic acid monotherapy group). A higher proportion of the ER nicotinic acid/laropiprant group discontinued treatment because of GI (2.5% vs. 1.5%) or laboratory adverse events (1.3% vs. 0.7%), particularly abnormal liver function test (LFT) results. In its Committee for Medicinal Products for Human Use assessment, the European Medicines Agency concluded that "the lower discontinuation rate due to flushing is partly offset by other side-effects in particular the occurrence of GI symptoms". Recipients of ER nicotinic acid/laropiprant might also experience a higher frequency of non-flushing adverse effects of nicotinic acid because they are able to achieve higher nicotinic acid doses without flushing.

Salicylic Acid

Inflammation and innate immunity have been implicated in the pathogenesis of insulin resistance and type 2 diabetes. Obesity activates the transcription of nuclear factor-kappa beta (NF-κβ) which promotes insulin resistance and risk for both type 2 diabetes and CVD. High doses of sodium salicylate inhibit NF-κβ. Additional methods that might contribute to the glucose lowering effects of salicylates include inhibition of cellular kinases, upregulation of the heat shock response and increased in circulating insulin concentrations.

Recent studies have investigated the hypoglycemic actions of salicylates. In one study both high dose (4.5 g daily in three divided doses (n=7)) and standard dose (3.0 g/daily in two divided doses (n=9)) salsalate was administered for two weeks. Fasting glucose levels fell by 19% (p<0.03) and 9% (p=0.05) in the high and standard dose groups respectively. There was a 19% reduction in glycated albumin with the 4.5 g dose (p=0.005). There was an improvement in fasting insulin levels in both cohorts, TG concentrations were decreased (40% at 4.5 g and 11% at 3.0 g) and total cholesterol fell by 12%. Dose limiting tinnitus occurred at the higher dose, and both doses were associated with a small but significant increase in serum creatinine Although no GI adverse events were reported, misoprostol 200 mcg was concurrently administered four times daily to prevent adverse GI effects. (Goldfine 2008).

In the second study the effect of 4.0 g salsalate (administered in two divided doses) was assessed in 20 obese non-diabetic adults after one month of treatment. Compared with placebo, salsalate reduced fasting glucose by 13% (p<0.002), glycemic response after an oral glucose challenge by 20% (p<0.004) and glycated albumin by 17% (p<0.003). Three participants required a dose reduction because of tinnitus, headache or dizziness. Two patients discontinued treatment due to rash. Again, there were no reports of GI toxicity (Fleischman 2008).

The TINSAL-T2D (Targeting Inflammation Using Salsalate in Type 2 Diabetes) published last year was the first RCT, designed to evaluate the safety, tolerability and efficaciousness of salsalate in patients with type 2 diabetes. Patients were randomly assigned to receive placebo, 3.0 g, 3.5 g or 4.0 g of salsalate daily (27 subjects in each group). Mean changes in HbA1c levels for the salsalate groups were −0.36% at 3.0 g (p=0.02), −0.34% at 3.5 g (p=0.02) and −0.49% at 4.0 g (p=0.001) compared with placebo. Fasting blood glucose and glycated albumin were also lowered. TG concentration also fell and adiponectin concentration was raised. Hypoglycemia was the most common side-effect observed. Mild GI symptoms (heartburn, nausea, vomiting or diarrhea) were more frequent among patients receiving salsalate (not dose-related). There was no evidence of GI bleeding. Other adverse effects included increased urinary albumin levels and tinnitus (Goldfine 2010).

Salsalate has been prescribed for decades to treat joint pain without serious safety concerns. GI side-effects have been reported with salsalate but they tend to occur early in therapy in patients with pre-existing GI disease (Souza 1985). It is also unknown whether the combination of high dose salsalate with other agents such as aspirin and nicotinic acid would be associated with an augmented GI risk.

As detailed above, nicotinic acid is the most effective pharmacological means to raise HDL cholesterol levels with increases of 15-35%. In addition to its effects on HDL cholesterol, nicotinic acid significantly reduces LDL cholesterol and TGs. However, clinical use of this drug is limited because of dose dependent adverse effects (mainly flushing). Hyperglycemia is another important side-effect associated with nicotinic acid therapy and 10-35% of diabetics treated with nicotinic acid will require a change in hypoglycemic therapy. Approximately 20% of patients experience GI symptoms, including diarrhea, nausea, vomiting, abdominal pain and dyspepsia are common.

Further, the combination of ER nicotinic acid and laropiprant (aPGD$_2$ antagonist) has been formulated into a single tablet (Tredaptive®) and has been licensed in Europe since July 2008. It improves the flushing tolerability of nicotinic acid; however, it does not provide benefits in terms of glycemic disturbance. In June 2008 the FDA advised the manufacturers that further efficacy and safety data was required and has delayed approval until the data from the HPS2-THRIVE study are available (which is not expected before 2013). As long-term safety data is available on nicotinic acid, the main obstacle to the US launch of Tredaptive® was the long-term safety of laropiprant.

Compounds and Compositions

Studies have shown that a majority of patients on an aspirin regimen also require treatment for dyslipidema. Correspondingly, a majority of patients treated for dyslipidemia are also prescribed aspirin. Furthermore, studies suggest that up to one third of the patient population suffering from dyslipidemia has pre-existing elevated fasting glucose and therefore is particularly vulnerable to the glycemic disturbance associated with nicotinic acid. Therefore, there remains a need to provide a nicotinic acid composition which does not produce side-effects such as flushing and hyperglycemia but which has an acceptable safety profile.

Accordingly, in one embodiment the present invention provides a composition for the treatment of dyslipidemia comprising nicotinic acid, aspirin and salicylic acid, and a pharmaceutically acceptable carrier or vehicle.

In some embodiments, the present invention provides an aspirin prodrug comprising a new molecular entity metabolized to aspirin, salicylic acid and nicotinic acid. In some such embodiments, the prodrug is isosorbide nicotinate aspirinate. The characteristics of isosorbide nicotinate aspirinate are well suited to the management of dyslipidaemia and adverse effects associated with high doses of niacin. As a prodrug, it is intrinsically inactive which should not cause topical GI toxicity associated with conventional aspirin; it is metabolized by BuChE and CE-2 in human plasma and liver releasing nicotinic acid which can provide improvements in dyslipidemia; it also releases known metabolites including aspirin and salicylic acid which might attenuate adverse effects of nicotinic acid; finally it should also attenuate platelet TxB2 production and provide antiplatelet efficacy in a patient population for whom this therapy is generally indicated (Antithrombotic Trialists 2009). Accordingly, in some embodiments, the present invention provides a composition which delivers therapeutically effective amounts of nicotinic acid, aspirin and salicylic acid without inducing GI toxicity. In some embodiments, the present invention provides a composition which delivers a GI-protective therapeutically effective amounts of nicotinic acid, aspirin and salicylic acid. In some embodiments, the present invention provides a composition comprising an equivalent daily dose less than 150 mg aspirin, an equivalent daily dose of about 2-3 g salicylic acid, and an equivalent daily dose of about 2 g nicotinic acid. In some embodiments, the present invention provides a composition comprising an equivalent daily dose of about 150-325 mg aspirin, an equivalent daily dose of about 2-3 g salicylic acid, and an equivalent daily dose of about 1-2 g nicotinic acid. In some embodiments, the present invention provides a composition comprising an equivalent daily dose of about 325-650 mg aspirin, an equivalent daily dose of about 2-3 g salicylic acid, and an equivalent daily dose of about 1-2 g nicotinic acid.

As described above, aspirin suppresses nicotinic acid-induced flushing by preventing the production of prostaglandins. Thus, it has been shown that aspirin can prophylactically treat nicotinic acid-induced flushing. Surprisingly, it has now been found that salicylic acid suppresses nicotinic acid-induced hyperglycemia. Therefore, in some embodiments, a provided composition comprising nicotinic acid, aspirin, and salicylic acid, comprises an amount of nicotinic acid sufficient to increase HDL levels and/or decrease LDL and TG levels, but which does not induce flushing. In certain embodiments, a provided composition comprises an amount of nicotinic acid sufficient to increase HDL levels and/or decrease LDL and TG levels, but which does not induce hyperglycemia. In some embodiments, a provided composition comprises an amount of nicotinic acid sufficient to increase HDL levels and/or decrease LDL and TG levels, but which does not induce either flushing or hyperglycemia.

In some embodiments, a composition of the present invention comprises an IR dose of aspirin, a delayed release dose of nicotinic acid, and salicylic acid. In some embodiments, a composition of the present invention comprises an IR dose of aspirin, a delayed release dose of nicotinic acid, and salicylic acid, wherein the aspirin dose is an equivalent daily dose is less than 1300 mg, the nicotinic acid dose is an equivalent daily dose of about 2 g, and the salicylic acid dose is an equivalent daily dose of about 3 g. In some embodiments, a composition of the present invention comprises an IR dose of aspirin, a delayed release dose of nicotinic acid, and salicylic acid, wherein the aspirin dose is an equivalent daily dose from 150-650 mg, the nicotinic acid dose is an equivalent daily dose of about 2 g, and the salicylic acid dose is an equivalent daily dose of about 3 g.

In some embodiments, a composition of the present invention comprises an IR dose of aspirin, a delayed release dose of nicotinic acid, and salicylic acid, wherein the salicylic acid dose is sufficient to reduce blood glucose levels at least 5%.

Although high dose nicotinic acid is an effective dyslipidemic agent and aspirin is effective in suppressing nicotinic acid-induced flushing by inhibiting $PGD_2$ synthesis, both of these agents cause significant GI toxicity. In fact, GI complications associated with NSAIDs cause more than 20,000 deaths and cost in excess of $4 billion. Doses as low as 10 mg can damage the GI, and more than 75% of patients will have at least occult bleeding with daily aspirin use even at low doses. Further, even enteric coated and buffered aspirin are also associated with GI toxicity.

Accordingly, in some embodiments the present invention provides a compound which delivers therapeutically effective amounts of nicotinic acid, aspirin and salicylic acid. In some embodiments the present invention provides a composition which delivers therapeutically effective amounts of nicotinic acid, aspirin and salicylic acid without inducing GI toxicity. In some embodiments, the present invention provides a method for treating dyslipidemia comprising administering compound I, or a pharmaceutically acceptable salt thereof:

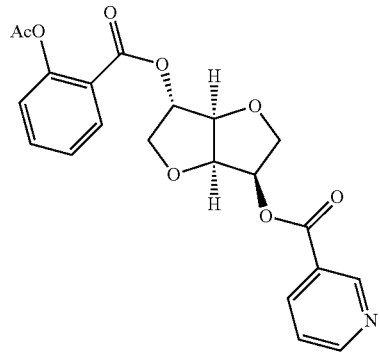

I

The metabolism of I is known to proceed along two distinct metabolic pathways, as shown in Scheme 1:

Scheme 1. Metabolism of isosorbide-2-acetylsalicylate-5-nicotinate.

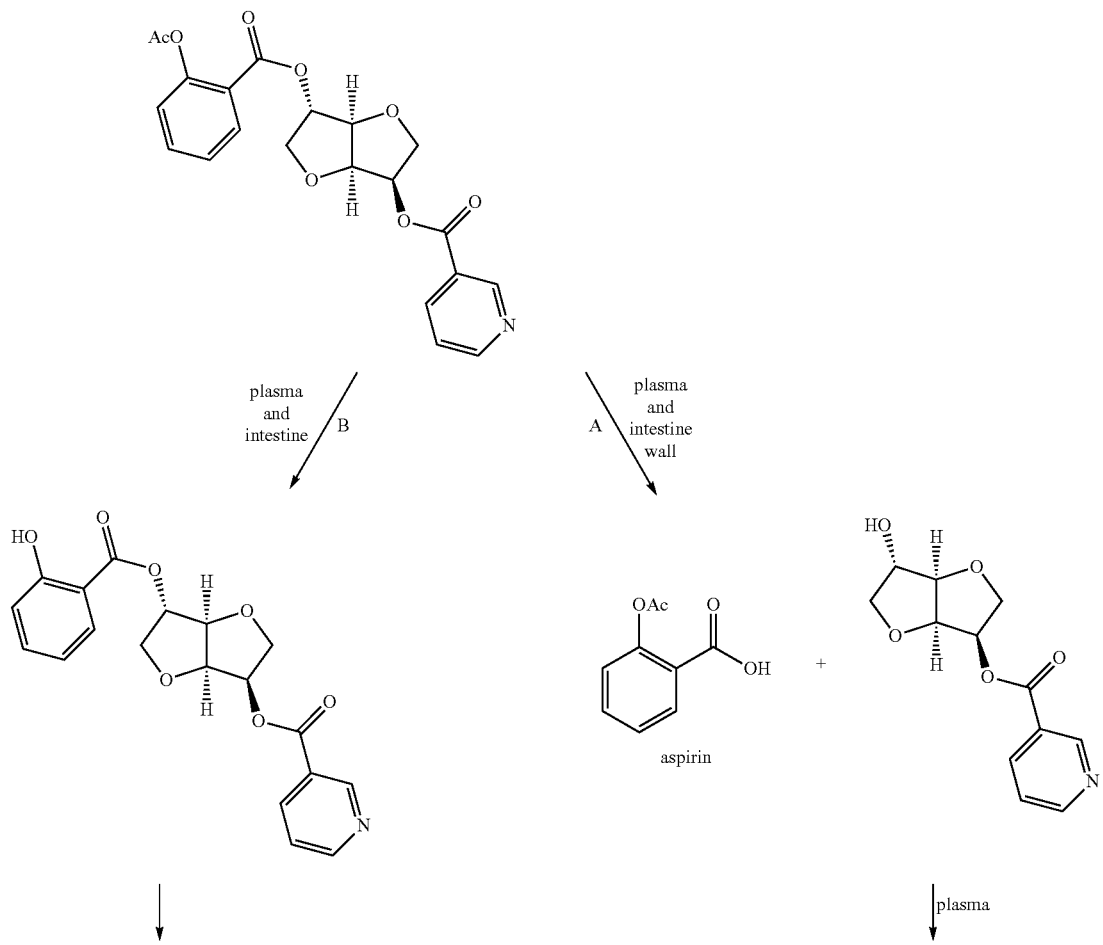

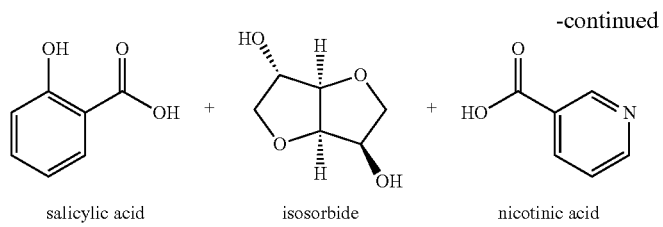

salicylic acid + isosorbide + nicotinic acid

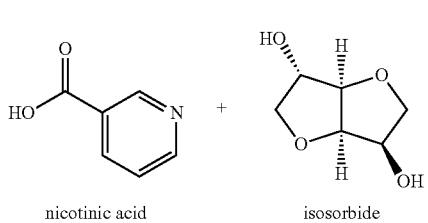

nicotinic acid + isosorbide

One of ordinary skill in the art will recognize that compound I effectively acts as a prodrug of nicotinic acid, salicylic acid, and aspirin.

As used herein, the term "prodrug" refers to a derivative of a parent drug molecule that requires transformation within the body in order to release the active drug, and that has improved physical and/or delivery properties over the active drug molecule. For example, and as depicted in Scheme 1, above, compound I is transformed by metabolic means to ultimately provide nicotinic acid, aspirin, and salicylic acid.

In contrast, the metabolism of aspirin and its esters is shown in Scheme 2.

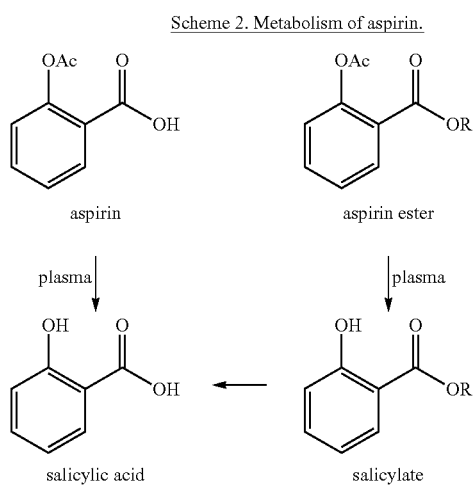

Scheme 2. Metabolism of aspirin.

Aspirin undergoes significant metabolism via O-deacetylation, generating salicylic acid. Aspirin esters are not metabolized to aspirin, as would be expected and desired, but are instead metabolized in a manner similar to aspirin —O-deacetylation followed by ester hydrolysis. Because the metabolism of aspirin esters does not proceed with ester hydrolysis, the significant metabolite of either aspirin or aspirin esters is salicylic acid.

It has now been found that isosorbide-2-acetylsalicylate-5-nicotinic acid (I) undergoes metabolism via two routes, A and B, as depicted in Scheme 1. The two competing metabolic pathways are nearly equivalent, such that nearly equal amounts of isosorbide-2-acetylsalicylate-5-nicotinic acid (I) are metabolized by both pathways. Instead of undergoing immediate O-deacetylation, as would be expected based on the metabolic profile of other aspirin esters, the aspirin prodrug isosorbide-2-acetylsalicylate-5-nicotinic acid (I) is metabolized at the acetylsalicylate ester first, releasing aspirin and isosorbide-nicotinate. This pattern yields an ideal plasma profile in primates with respect to aspirin, salicylic acid and nicotinic acid.

In both metabolic pathways, nicotinic acid is released after the salicylic acid or aspirin moieties. Isosorbide-2-acetylsalicylate-5-nicotinic acid (I) provides an immediate release of aspirin or salicylic acid, followed by a delayed release of nicotinic acid. The early release of both aspirin and salicylic acid provides a preventative measure against flushing and hyperglycemia normally associated with the administration of nicotinic acid. Therefore, in one embodiment, the present invention provides a composition which provides a delayed release of nicotinic acid. In some embodiments, the present invention provides a composition comprising isosorbide-2-acetylsalicylate-5-nicotinic acid (I).

A composition comprising a molar equivalent of nicotinic acid and aspirin would not be expected to be clinically useful if both moieties were released in a 1:1 ratio, as the optimal therapeutically effective amounts of aspirin and nicotinic acid vary greatly. The daily therapeutic amount of nicotinic acid is about 1-2 g. Conversely, the recommended daily therapeutic amount of aspirin is significantly smaller, from about 75 mg. Therefore, to provide a therapeutically effective amount of nicotinic acid, one would need to administer a large amount of isosorbide-2-acetylsalicylate-5-nicotinic acid (I). However, an amount of isosorbide-2-acetylsalicylate-5-nicotinic acid (I) sufficient to deliver 1-2 g of nicotinic acid would deliver an overdose of aspirin. Conversely, an amount of isosorbide-2-acetylsalicylate-5-nicotinic acid (I) sufficient to deliver 75 mg of aspirin would deliver a therapeutically ineffective dose of nicotinic acid. Therefore, based on the therapeutically effective amounts required for both nicotinic acid and aspirin, one would conclude that the isosorbide-2-acetylsalicylate-5-nicotinic acid (I) structure was incapable of delivering optimal doses of either moiety.

It has been surprisingly found that the resulting metabolic profile for isosorbide-2-acetylsalicylate-5-nicotinic acid (I) provides a 0.2-0.4 molar equivalent aspirin, 1 molar equivalent of salicylic acid (0.2-0.4 from aspirin metabolism) and 1.0 molar equivalent of nicotinic acid. This ratio is unexpected because of the high propensity of aspirin to undergo O-deactylation to salicylic acid. In fact, the metabolism of aspirin esters has been widely studied in an attempt to create aspirin prodrugs which would not irritate the stomach lining. However, when aspirin esters are subjected to metabolic enzymes post-absorption, the aspirin esters do not undergo hydrolysis of the benzoic ester but instead undergo O-deactylation to salicylate esters. Further, the partial O-deacetylation of either aspirin or isosorbide-2-acetylsalicylate-5-nicotinic acid (I) delivers a high dose of salicylic acid, which mitigates the insulin sensitivity and corrects the impairment of glucose tolerance associated with high doses of nicotinic acid. Therefore, it is surprising and unexpected that the aspirin ester isosorbide-2-acetylsalicylate-5-nicotinic acid (I) undergoes significant ester hydrolysis in plasma, thereby releasing therapeutic amounts of aspirin and salicylic acid while also releasing therapeutic amounts of nicotinic acid.

Further, because the metabolism of isosorbide-2-acetylsalicylate-5-nicotinic acid (I) takes place in either the plasma or intestinal wall, the liberation of aspirin and nicotinic acid does not contact the stomach lining, as the compound has already passed through the stomach. Therefore, stomach irritation is not observed with the administration of isosorbide-2-acetylsalicylate-5-nicotinic acid (I). Accordingly, in some embodiments, the present invention provides a composition comprising isosorbide-2-acetylsalicylate-5-nicotinic acid (I) wherein the composition does not induce GI toxicity. In some embodiments, the present invention provides a composition comprising isosorbide-2-acetylsalicylate-5-nicotinic acid (I) wherein the composition protects the gastrointestinal mucosa from irritation and inflammation.

Additionally, the metabolic products of isosorbide-2-acetylsalicylate-5-nicotinic acid (I) are well-known pharmacological entities with predictable safety and efficacy profiles.

In some embodiments, a composition of the present invention further comprises an additional therapeutic agent or is administered in combination with an additional therapeutic agent. In some embodiments, the therapeutic agent is a statin, a bile acid sequestrant, or a fibric acid derivative.

As used herein, the term "combination" refers to simultaneous or sequential administration of agents. The term "combination" also refers to administration of agents formulated in one or more single unit dosage forms.

In some embodiments, a composition of the present invention further comprises, or is administered in combination with, a statin, wherein the statin is selected from the group consisting of atorvastatin, fluvastatin, lovastatin, pravastatin, rosuvastatin and simvastatin. In some embodiments, a composition of the present invention further comprises a bile acid sequestrant, wherein the bile acid sequestrant is selected from the group consisting of colesevelam, cholestyramine and colestipol. In some embodiments, a composition of the present invention further comprises a fibric acid derivative, wherein the fibric acid derivative is selected from the group consisting of gemfibrozil, fenofibrate and clofibrate. In some embodiments, a composition of the present invention further comprises a cholesterol absorption inhibitor, wherein the cholesterol absorption inhibitor is ezetimibe.

In some embodiments, a composition of the present invention further comprises, or is administered in combination with, an angiotensin-converting enzyme (ACE) inhibitor, wherein the ACE inhibitor is selected from the group consisting of enalapril, captopril, zofenopril, ramipril, quinapril, perindopril, lisinopril, benazepril, moexipril, trandolapril and fosinopril.

In some embodiments, a composition of the present invention further comprises, or is administered in combination with, one or more additional therapeutic agents selected from the group consisting of hydroxy-substituted azetidinone compounds, substituted β-lactam compounds, HMG CoA reductase inhibitor compounds, HMG CoA synthetase inhibitors, squalene synthesis inhibitors, squalene epoxidase inhibitors, sterol biosynthesis inhibitors, nicotinic acid derivatives, bile acid sequestrants, inorganic cholesterol sequestrants, Acyl-CoA:cholesterol O-acyltransferase inhibitors, cholesteryl ester transfer protein inhibitors, fish oils containing Omega 3 fatty acids, natural water soluble fibers, plant sterols and/or fatty acid esters of plant sterols, anti-oxidants, PPAR-agonists, PPAR-agonists, FXR receptor modulators, LXR receptor agonists, lipoprotein synthesis inhibitors, renin angiotensin inhibitors, microsomal triglyceride transport protein inhibitors, bile acid reabsorption inhibitors, PPAR-agonists, triglyceride synthesis inhibitors, low density lipoprotein receptor inducers or activators, platelet aggregation inhibitors, 5-LO or FLAP inhibitors, PPAR partial agonists, niacin or niacin receptor agonists, 5HT transporter inhibitors, NE transporter inhibitors, $CB_1$ antagonists/inverse agonists, ghrelin antagonists, $H_3$ antagonists/inverse agonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, leptin derivatives, opiod antagonists, orexin receptor antagonists, BRS3 agonists, CCK-A agonists, CNTF, CNTF derivatives, CNTF agonists/modulators, 5HT2c agonists, Mc4r agonists, monoamine reuptake inhibitors, serotonin reuptake inhibitors, GLP-1, GLP-1 agonists, GLP-1 mimetics, phentermine, topiramate, phytopharm compound 57, ghrelin antibodies, Mc3r agonists, ACC inhibitors, b3 agonists, DGAT1 inhibitors, DGAT2 inhibitors, FAS inhibitors, PDE inhibitors, thyroid hormone agonists, UCP-1 activators, UCP-2 activators, UCP-3 activators, acyl-estrogens, glucocorticoid agonists/antagonists, 11 HSD-1 inhibitors, SCD-1 inhibitors, lipase inhibitors, fatty acid transporter inhibitors, dicarboxylate transporter inhibitors, glucose transporter inhibitors, phosphate transporter inhibitors, anti-diabetic agents, anti-hypertensive agents, anti-dyslipidemic agents, DP receptor antagonists, apolipoprotein-B secretion/microsomal triglyceride transfer protein (apo-B/MTP) inhibitors, sympathomimetic agonists, dopamine agonists, melanocyte-stimulating hormone receptor analogs, melanin concentrating hormone antagonists, lepton, galanin receptor antagonists, bombesin agonists, neuropeptide-Y antagonists, dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, MSH-receptor analogs, -glucosidase inhibitors, apo A1 milano reverse cholesterol transport inhibitors, fatty acid binding protein inhibitors (FABP), and fatty acid transporter protein inhibitors (FATP).

Uses, Formulation and Administration
1. Pharmaceutically Acceptable Compositions According to another embodiment, the invention provides a composition comprising nicotinic acid, aspirin, salicylic acid, or a pharmaceutically acceptable salt thereof, and a pharmaceutically acceptable carrier, adjuvant, or vehicle.

In some embodiments, the invention provides a composition comprising compound I and a pharmaceutically acceptable derivative thereof and a pharmaceutically acceptable carrier, adjuvant, or vehicle. In certain embodiments, the amount of compound or compounds in a provided composition is such that is effective to measurably decrease LDL or TG levels and/or increase HDL levels in a biological sample or in a patient. In certain embodiments, a provided composition is formulated for administration to a patient in need of such composition. In some embodiments, a composition of this invention is formulated for oral administration to a patient.

The term "patient", as used herein, means an animal, preferably a mammal, and most preferably a human.

The term "biological sample", as used herein, includes, without limitation, cell cultures or extracts thereof biopsied material obtained from a mammal or extracts thereof and blood, saliva, urine, feces, semen, tears, or other body fluids or extracts thereof.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

The amount of compounds of the present invention that may be combined with the carrier materials to produce a composition in a single dosage form will vary depending upon the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

2. Uses of Compounds and Pharmaceutically Acceptable Compositions

Compounds and compositions described herein are generally useful for treating dyslipidemia. As described generally above, dyslipidemia is a general term for a disruption in the amount of lipids in the blood. Dyslipidemia is most often referred to as hyperlipidemia, or increased levels of lipids such as cholesterol in the blood. Hyperlipidemia can be classified by phenotype or etiology. There are six different phenotypes of hyperlipidemia. The most common phenotypes, IIa and IIb, are associated with increased lipoprotein LDL levels. Phenotypes IIb and IV are associated with increased lipoprotein VLDL (very low density lipoprotein). Patients who suffer from type IIb hyperlipidemia overproduce TGs. Type IV is also known as hypertriglyceridemia, due to the high levels of TGs (>200 mg/dl) produced in the subset of patients suffering therefrom.

Accordingly, in some embodiments, a composition of the present invention is useful for measurably decreasing LDL levels in a biological sample or in a patient. In some embodiments, a composition of the present invention is useful for measurably decreasing TG levels in a biological sample or in a patient. Thus, in some embodiments, the present invention provides a method for treating dyslipidemia comprising administering to a patient in need thereof, an effective amount of nicotinic acid, aspirin, and salicylic acid, or a salt thereof. One of ordinary skill in the art will recognize that nicotinic acid, aspirin, and salicylic acid can be administered as a composition comprising nicotinic acid, aspirin, and salicylic acid in a single unit dosage form. Alternatively, nicotinic acid, aspirin, and salicylic acid can be administered individually, either simultaneously or sequentially.

In certain embodiments, the present invention provides a method for measurably decreasing TG levels in a biological sample or in a patient, comprising contacting the biological sample, or administering to the patient, compound I or a composition thereof.

Dyslipidemia can also refer to hypolipidemia, or a decrease in blood lipid levels. Most notably, hypolipidemia describes the abnormally low levels of HDL. HDL is the smallest of the lipoproteins, and is implicated in the transport of cholesterol back to the liver for excretion or re-utilization. HDL is the densest of the lipoproteins because it contains the highest proportion of protein. HDL is beneficial and high levels are known to be protective against CV diseases such as ischemic stroke and MI. Accordingly, in some embodiments, a composition of the present invention is useful for measurably increasing HDL levels in a biological sample or in a patient. In some embodiments, a composition of the present invention is useful for measurably increasing HDL levels above 60 mg/dL in a biological sample or in a patient. In some embodiments, a composition of the present invention is useful for measurably increasing HDL levels above 50 mg/dL in a biological sample or in a patient. In some embodiments, a composition of the present invention is useful for measurably increasing HDL levels above 40 mg/dL in a biological sample or in a patient.

EXEMPLIFICATION

Example 1

Figure 1:
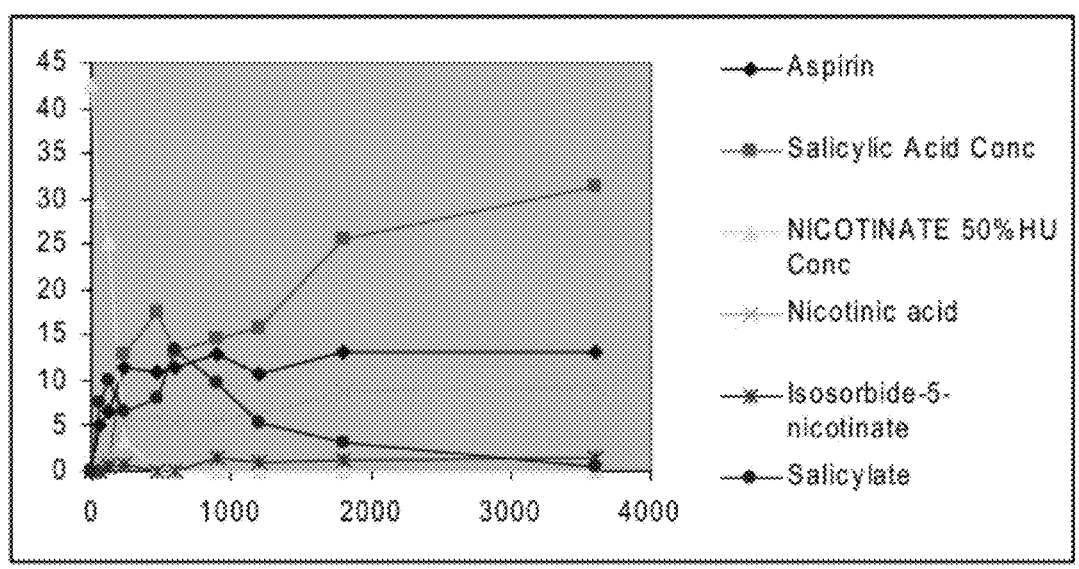

FIG. 1 depicts a progress curve for the disappearance of isosorbide-2-aspirinate-5-nicotinate (ST0702) following incubation (in vitro) in 50% human plasma diluted with pH 7.4 buffer at 37° C. ST0702 undergoes rapid conversion to a series of hydrolysis products as a result of the actions of butyrylcholinesterase in plasma. The products are aspirin, isosorbide-2-salicylate-5-nicotinate (salicylate), salicylic acid (a hydrolysis product of the salicylate) leading to formation of isorobide-5-nicotinate and eventually nicotinic acid.

Hydrolysis and Enzyme Studies

Detection of hydrolysis of ST0702 aspirin, isosorbide-2-salicylate-5-nicotinate (salicylate), salicylic acid (a hydrolysis product of the salicylate) leading to formation of isosorbide-5-nicotinate and eventually nicotinic acid was performed by high performance liquid chromatography using a system consisting of a Waters 600E pump and controller, a Waters 717 Autosampler and a Waters (2)996 PDA all controlled by Millennium or Alliance Chromatography Manager. A Waters Spherisorb® (4 µm) C18 3.9×250 mm column was used for the plasma and enzyme study samples. The enzyme and plasma study samples were analysed using a gradient method employing a mobile phase consisting of pH 3.19 phosphate buffer:acetonitrile 90:10 grading to 10:90 over the first ten minutes then back to 65:35 to 12 minutes and grading to 90:10 to 17 minutes at which it was held to 30 minutes. The eluent in both methods was monitored at 230 nm and peak identity and homogeneity confirmed by PDA analysis. Quantitation was performed by comparison of peak areas with external standards run under the same conditions at about the same concentration. The flow rate was 1 ml/min.

For the hydrolysis experiments pooled plasma or serum solutions (4 ml) were prepared by centrifugation of citrated human venous blood and dilution with pH 7.4 phosphate buffer as appropriate. Whole blood was used undiluted. The test compounds in acetonitrile (100 µl) were incubated in (4 ml) of the preheated solution (37±0.5° C.) at a concentration of $5 \times 10^{-5}$ M and 250 µl aliquots withdrawn at appropriate intervals. Samples were transferred to 1.5 ml Eppendorf tubes containing 500 µA of a 2% $ZnSO_4 \cdot 7H_2O$ in MeCN—$H_2O$ (1:1) solution, vortexed and then centrifuged for 4 minutes at 10,000 rpm. 20 µl aliquots of the supernatant were analysed by HPLC. Hydrolysis was monitored until consumption of the parent ester. The hydrolysis experiments were repeated in the presence of the following inhibitors which were incubated in the buffered plasma solution for five minutes before addition of the ester solution: EDTA (2 mM), BNPP (10 µM), eserine (20 µM), BW254c51 (0.1-100 µM), dibucaine (20 µM), isoOMPA (10 µM). The samples were then processed as above. All experiments were performed in triplicate. Cholinesterase activity of plasma, serum and whole blood was evaluated using the Ellman approach with butyryl thiocholine as substrate. Values were typically between 2200 and 4000 nmoles/ml plasma/min. The hydrolysis was evaluated in the presence of purified horse serum BuChE (Sigma) at a concentration of 0.1 mg/ml (1,000 units/mg protein) in phosphate buffer (pH 7.4) and in the presence of purified human serum BuChE 0.1 mg/ml (14 units/mg protein) (SIGMA). The activity of these preparations was confirmed using the Ellman assay with butyrylthiocholine as substrate.

Example 2

Figure 2:
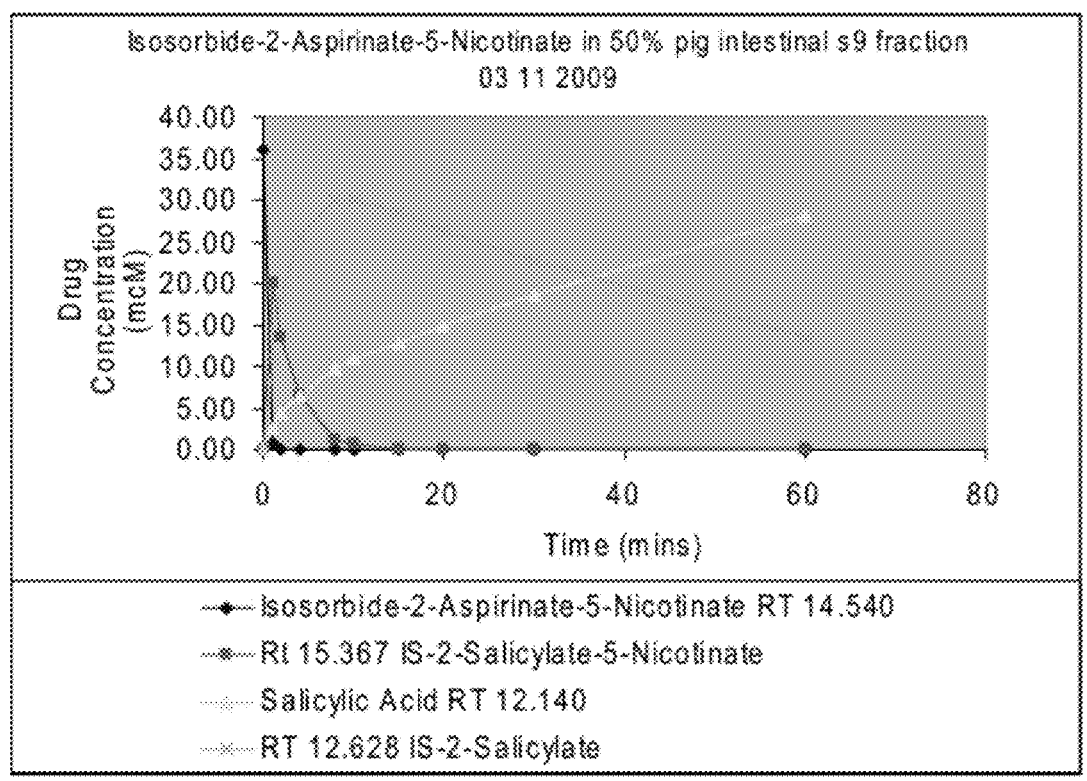
FIG. 2 depicts a progress curve for the disappearance of ST0702 following incubation with pig intestinal S9 fraction. This experiment illustrates that the enzymes of human plasma are suited to producing aspirin from ST0702 whereas enzymes from other sources including pig intestine do not produce aspirin (rat, rabbit and mouse intestinal preparations also do not produce aspirin).

FIG. 2 depicts a progress curve for the disappearance of ST0702 following incubation with pig intestinal S9 fraction. This experiment illustrates that the enzymes of human plasma are suited to producing aspirin from ST0702 whereas enzymes from other sources including pig intestine do not produce aspirin (rat, rabbit and mouse intestinal preparations also do not produce aspirin).

Incubation of ST0702 with pig intestinal S9 fraction was performed was performed in a manner substantially similar to that described in detail in Moriarty et al., "Discovery of a "True" Aspirin Prodrug," *J. Med. Chem.* 2008 51, 7991-7999 and Gilmer et al., "Isosorbide-based aspirin prodrugs II. Hydrolysis kinetics of isosorbide diaspirinate," *Eur. J. Pharm. Sciences* 16 2002 297-304.

Analysis of the incubation for presence of ST0702 was performed as described above for Example 1.

Example 3

Figure 3:
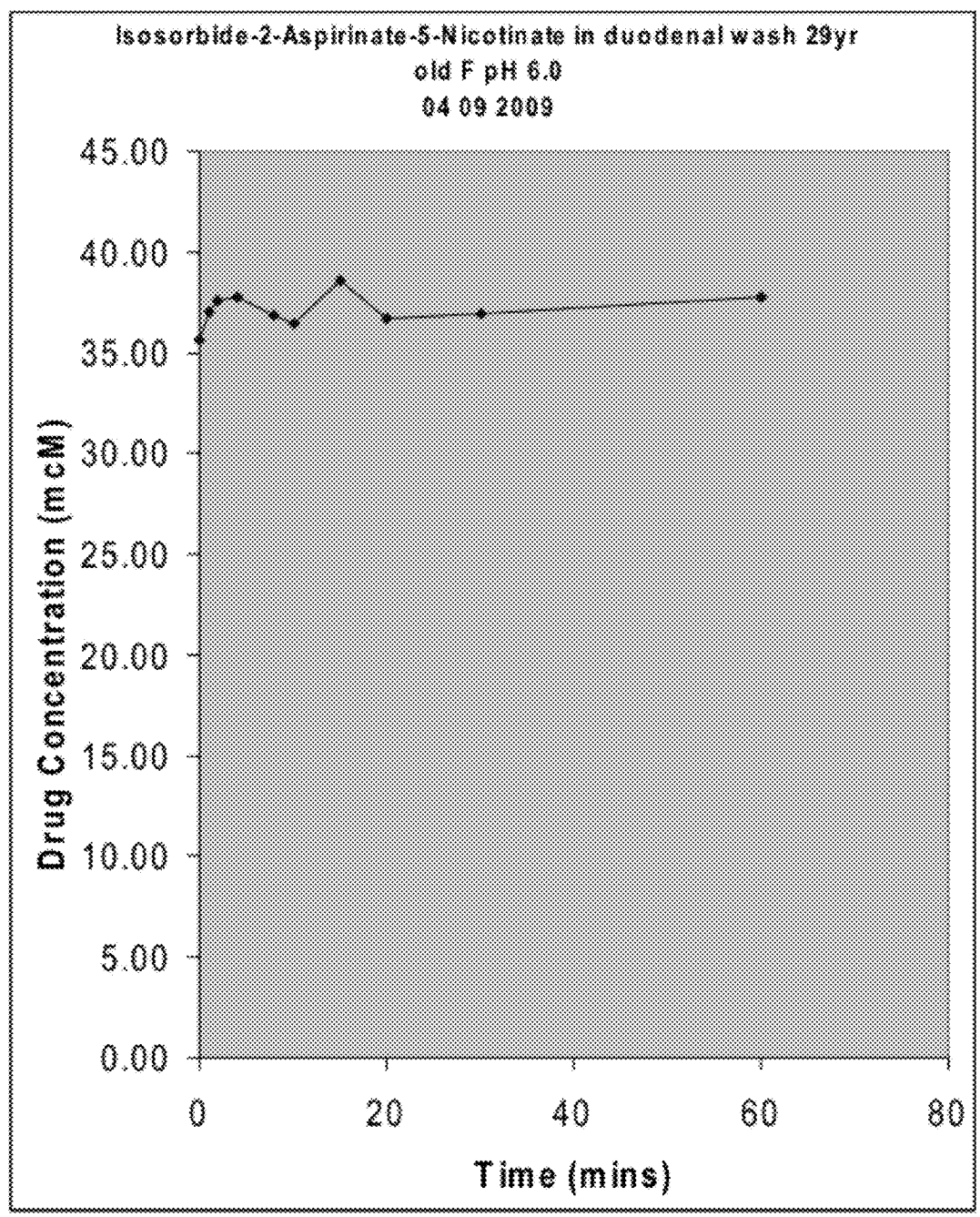
FIG. 3 depicts a progress curve following incubation of ST0702 in diluted human intestinal contents, demonstrating that ST0702 is effectively unchanged after a prolonged period of time in contact with human intestinal contents and therefore is suitable for oral administration.

FIG. 3 depicts a progress curve following incubation of ST0702 in diluted human intestinal contents, demonstrating that ST0702 is effectively unchanged after a prolonged period of time in contact with human intestinal contents and therefore is suitable for oral administration.

Incubation of ST0702 in diluted human intestinal contents was performed was performed in a manner substantially similar to that described in detail in Moriarty et al., "Discovery of a "True" Aspirin Prodrug," *J. Med. Chem.* 2008 51, 7991-7999 and Gilmer et al., "Isosorbide-based aspirin prodrugs II. Hydrolysis kinetics of isosorbide diaspirinate," *Eur. J. Pharm. Sciences* 16 2002 297-304.

Analysis of the incubation for presence of ST0702 was performed as described above for Example 1.

Example 4

Figure 4:
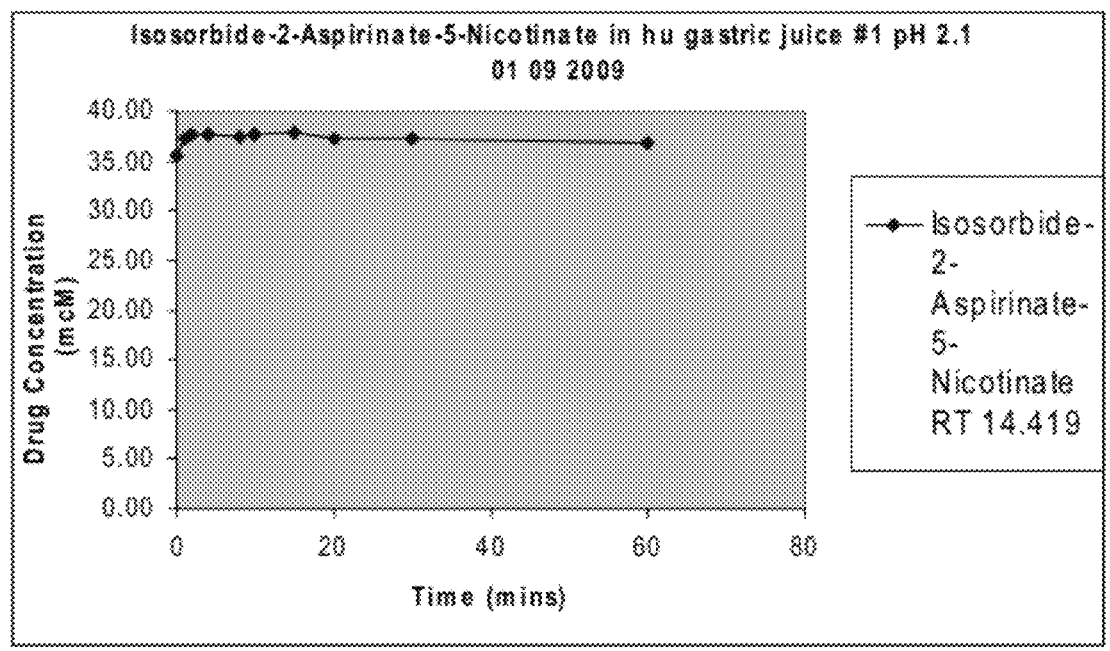
FIG. 4 depicts a graph which shows the incubation of ST0702 in human gastric juice. ST0702 is not metabolized over 60 minutes, indicating that it could survive passage through the stomach and enter the intestine/intestinal wall intact.

FIG. 4 depicts a graph which shows the incubation of ST0702 in human gastric juice. ST0702 is not metabolized over 60 minutes, indicating that it could survive passage through the stomach and enter the intestine/intestinal wall intact.

Incubation of ST0702 in human gastric juice was performed was performed in a manner substantially similar to that described in detail in Moriarty et al., "Discovery of a "True" Aspirin Prodrug," *J. Med. Chem.* 2008 51, 7991-7999 and Gilmer et al., "Isosorbide-based aspirin prodrugs II. Hydrolysis kinetics of isosorbide diaspirinate," *Eur. J. Pharm. Sciences* 16 2002 297-304.

Analysis of the incubation for presence of ST0702 was performed as described above for Example 1.

Example 5

FIGS. 5 and 6 depict graphs demonstrating the incubation of ST0702 in the presence of human liver microsomes.

Incubation of ST0702 in the presence of human liver microsomes was performed was performed in a manner substantially similar to that described in detail in Moriarty et al., "Discovery of a "True" Aspirin Prodrug," *J. Med. Chem.* 2008 51, 7991-7999 and Gilmer et al., "Isosorbide-based aspirin prodrugs II. Hydrolysis kinetics of isosorbide diaspirinate," *Eur. J. Pharm. Sciences* 16 2002 297-304.

Analysis of the incubation for presence of ST0702 was performed as described above for Example 1.

Example 6

FIG. 7 depicts a progress curve following incubation of ST0702 in the presence of microsomes from the human intestinal wall. These contain most carboxylesterase-2 which causes hydrolysis predominantly at the isosorbide-2-position liberating aspirin and isosorbide-5-nicotinate.

Incubation of ST0702 in the presence of microsomes from the human intestinal wall was performed in a manner substantially similar to that described in detail in Moriarty et al., "Discovery of a "True" Aspirin Prodrug," *J. Med. Chem.* 2008 51, 7991-7999 and Gilmer et al., "Isosorbide-based aspirin prodrugs II. Hydrolysis kinetics of isosorbide diaspirinate," *Eur. J. Pharm. Sciences* 16 2002 297-304.

Analysis of the incubation for presence of ST0702 was performed as described above for Example 1.

Example 7

Ulcerogenic effects of aspirin and aspirin pro-drugs ST0701, ST0702, and ST0703 were determined in rabbits using the following procedure. Healthy female rabbits (n=2 per group) were dosed (by oral gavage) for 3 consecutive days with 30 mg/kg of aspirin or the molar equivalent of ST0702 and the other pro drugs. Four hours post-dose on the final day, the rabbits were euthanized using an overdose of pentobarbitone and their stomachs and small intestine removed, washed with physiological saline, opened along the greater curvature and examined. The area (square millimeters) of both non-haemorrhagic and haemorrhagic lesions developed in the stomach/intestines were measured with a square grid under a dissecting microscope. The average area of lesions developed is presented in FIG. 15.

Example 8

This study aims to evaluate for the first time isosorbide-5-nicotinate-2-aspirinate on markers of niacin efficacy and safety and TxB2 production in non-human primates (NHPs). The NHP model was chosen because pre-clinical evaluation of pro-drugs should preferably occur in non-human primates because of lack of esterase homology between humans and lower order animals.

In-Vivo Study Design.

Studies were carried out by contract research organization Charles River, Shanghai, China. A total of 6 purpose bred, NHPs (cynomologus monkeys, weight 2.8 to 4.5 kg) were sourced and randomly allocated in a 3 step crossover design to 3 test articles (n=6 per group): ST0702 and niacin at high dose, equimolar amounts (28 mg/kg niacin equivalents) and control. A washout period of at least 2 weeks occurred between crossover phases. Animals were dosed daily by oral gavage in aqueous vehicle (below) over a 48 hour period.

The cynomolgus monkey was chosen for this study as it is a species that has shown pharmacologic responses to niacin on LDL cholesterol and ApoB and is a species that is commonly used for nonclinical pharmacokinetic and pharmacodynamic evaluations. Furthermore, use of NHP models maximizes the likelihood of identifying responses that are similar to those which may be expected in humans.

Each animal was identified by a cage label and body tattoo and was acclimated to oro-gastric dosing on at least 2 occasions prior to the initiation of dosing. The vehicle, 1% (w/v) Tween 80 and 0.5% (w/v) Carboxymethylcellulose in Deionized Water and 28 mg/Kg niacin molar equivalent of ST0702 (times 24, 48 hours) at times 0 and 24 hours using an orogastric tube inserted into the mouth and advanced into the stomach. The animals were temporarily restrained (e.g., manually) for dose administration, and were not sedated. Disposable sterile syringes and orogastric tubes were used for each animal/dose. Each dose was followed by a tap water flush of approximately 5 mL. Blood samples were taken at the following timepoints: pre-dose (0 hours) and at 0.083, 0.25, 0.50, 1, 2, 4, 12, 24, 48 hours after first administration of test article.

Effects of ST0702 and Niacin on LDL-C, Apo B Levels on 2 Day Oral Gavage Administration of Test Article in Non-Human Primates.

The primary study endpoint is change in plasma LDL cholesterol and Apolipoprotein B at 48 hours. An aliquot of 300 µL of serum transferred to a cryovial and was immediately placed in a freezer set to maintain −70° C. until analyzed for clinical chemistry (LDL cholesterol, Apolipoprotein B, TGs, glucose) using a standard Roche Analyser.

Plasma Profiles of Aspirin, Niacin and Salicylic Acid Following Administration of Equimolar Doses of ST0702 and Niacin by Daily Oral Gavage Administration of Test Article Over 48 Hours in Non-Human Primates.

Relative pharmacokinetic profiles of aspirin, salicylic acid and niacin in the plasma and respective area under the curve (AUC) measurements over the initial 24 hour period. For this additional 0.4 mL serum aliquots were placed in K2EDTA tubes and processed to plasma PK analysis using liquid chromatography mass spectroscopy methods.

Effects of ST0702 and Niacin on TxB2, PGD2 Levels Following Administration of Equimolar Doses of ST0702 and Niacin by Daily Oral Gavage Administration of Test Article Over 48 Hours in Non-Human Primates.

Relative effects of ST0702 and niacin on ex-vivo TxB2 and serum PGD2 levels were determined based on inhibition of baseline levels (TxB2) and total AUC measurements over the initial 24 hour period. For TxB2, an additional 0.4 mL whole blood aliquots were placed in siliconised glass tubes to induce a clotting response and the supernatants were analysed for TxB2 using a Luminex ELISA immunoassay. PGD2 was analysed from serum directly using a Luminex ELISA immunoassay.

Results. Clinical Chemistry:

Effects of ST0702, nicotinic acid (niacin), control on Apolipoprotein B and LDL cholesterol are presented in FIGS. 9A and 9B, respectively and show a better 53% and 42% reduction from baseline in LDL cholesterol (p=0.012) and apolipoprotein B (p=0.011) respectively with ST0702 compared with a 33% and 24% reduction in LDL cholesterol (p=0.02) and apolipoprotein B (p=0.098) respectively versus with ST0702 (p=0.097 for between group change). Changes versus control reached statistical significance only in the case of ST0702 on both biomarkers. TG levels were highly variable and showed non-significant increases of 11.3%, 4.4% and 23.3% in control, ST0702 and nicotinic acid (niacin) groups respectively (all p=NS within group changes). ST0702 TG levels were 59±29 mg/dL at baseline and 55±24 mg/dL at 48 hours whereas nicotinic acid (niacin) levels were 50±10 mg/dL at baseline and 64±31 mg/dL at follow up (p=0.033 between group change ST0702 vs nicotinic acid).

Serum glucose levels over the first 24 hours following dosing were monitored and are presented in FIG. 10. They demonstrated a significant decrease in glucose levels from baseline at 1 hour in both groups and a rebound to baseline levels following animal feeding between 1-2 hours post dose in the nicotinic acid (niacin) group, but not in the ST0702 group. At 4 hours plasma glucose levels remained below baseline levels (p=0.028) and also demonstrated a non-significant within group difference compared to nicotinic acid (niacin). This pattern appeared to persist at 12 hours, albeit without within or between group statistical significance.

Pharmacokinetic Profiles.

The ST0702 comparative pharmacokinetic profiles of plasma aspirin (FIG. 11A) nicotinic acid (niacin) (FIG. 11B) and salicylic acid (FIG. 11C) are presented for both test articles. The $T_{max}$ values determined for aspirin, nicotinic acid (niacin) and salicylic acid for ST0702 are 15 mins, 1 hour and 1 hour respectively. The $C_{max}$ values determined for aspirin, nicotinic acid (niacin) and salicylic acid for ST0702 are 1.056 µg/mL, 10.728 µg/mL and 42.256 µg/mL respectively. In a separate analysis of n=3 monkeys dosed with equimolar amounts of aspirin, the AUC value for the aspirin group was 14.01±1.02 µg/mL·hr compared with 3.50±0.64 µg/mL·hr for ST0702. This represents an exposure to aspirin of approximately 21% of the absolute amount of aspirin dosed and equivalent to a daily dose of just under approximately 9 mg/kg. In human dose equivalents, assuming a 70 kg average weight, this corresponds to a 630 mg daily dose. Although the $C_{max}$ for nicotinic acid (niacin) was higher in the nicotinic acid (niacin) group, the differences were non-significant and total nicotinic acid (niacin) AUC values were non-significantly higher at 20.65±9.71 µg/mL·hr for the nicotinic acid (niacin) group compared with 15.82±9.09 µg/mL·hr for ST0702 (p=0.39). Total salicylic acid AUC values were higher at 515.8±72.8 µg/mL·hr compared with 336.6±23.7 µg/mL·hr for ST0702 (p=0.012) indicating that 65% of the total salicylic acid in ST0702 was absorbed.

Immunochemistry.

Serum TxB2 levels (FIG. 12) were significantly reduced within the ST0702 group (all p<0.01) and between nicotinic acid (niacin) and ST0702 groups (all p<0.01) from 15 minutes on. Serum TxB2 suppression remained >95% at 24 and 48 hours in the ST0702 group.

The impact of nicotinic acid (niacin) and equimolar amounts of ST0702 on PGD2 levels are presented in FIG. 13 and show an 8 fold reduction in PGD2 AUC levels with ST0702 compared to nicotinic acid (niacin) treated animals (16.2±6.4 ng/mL·hr versus 128.3±38.2 ng/mL·hr respectively, p=0.012).

LIST OF REFERENCES

Abbott Laboratory Ireland Limited (2009). Summary of Product Characteristics: Niaspan, Medicines. ie.

Adult Treatment Panel. Third Report on the National Cholesterol Eduction Progran (NCEP) (2002). "Expert Panel on Detection, Evaluation and Treatment of High Blood Cholesterol in Adults (Adult Treatment Panel III) Final Report." Circulation 106(25): 3143-3421.

Antithrombotic Trialists Colloboration (2002). "Collaborative meta-analysis of randomised trials of antiplatelet therapy for prevention of death, myocardial infarction, and stroke in high risk patients." BMJ 324(7329): 71-86.

Antithrombotic Trialists, C. (2009). "Aspirin in the primary and secondary prevention of vascular disease: collaborative meta-analysis of individual participant data from randomised trials." The Lancet 373(9678): 1849-1860.

Avorn, J., J. Monette, et al. (1998). "Persistence of Use of Lipid-Lowering Medications." JAMA: The Journal of the American Medical Association 279(18): 1458-1462.

Baigent, C. (2005). "Efficacy and safety of cholesterol-lowering treatment: prospective meta-analysis of data from 90056 participants in 14 randomised trials of statins." The Lancet 366(9493): 1267-1278.

Barter, P. J., M. Caulfield, et al. (2007). "Effects of Torcetrapib in Patients at High Risk for Coronary Events." N Engl J Med 357(21): 2109-2122.

Benner, J. S., R. J. Glynn, et al. (2002). "Long-term Persistence in Use of Statin Therapy in Elderly Patients." JAMA: The Journal of the American Medical Association 288(4): 455-461

Brown, B. G., X.-Q. Zhao, et al. (2001). "Simvastatin and Niacin, Antioxidant Vitamins, or the Combination for the Prevention of Coronary Disease." N Engl J Med 345(22): 1583-1592.

Campbell, C. L., S. Smyth, et al. (2007). "Aspirin Dose for the Prevention of Cardiovascular Disease: A Systematic Review." *JAMA* 297(18): 2018-2024.

Canner, P. L., K. G. Berge, et al. (1986). "Fifteen year mortality in Coronary Drug Project patients: long-term benefit with niacin." *J Am Coll Cardiol* 6: 1245-1255.

Capuzzi, D., J. Morgan, et al. (2000). "Niacin dosing: Relationship to benefits and adverse effects." *Current Atherosclerosis Reports* 2(1): 64-71.

Castelli, W. P., R. J. Garrison, et al. (1986). "Incidence of Coronary Heart Disease and Lipoprotein Cholesterol Levels: The Framingham Study." *JAMA* 256(20): 2835-2838.

Cefali, E. A., P. D. Simmons, et al. (2007). "Aspirin reduces cutaneous flushing after administration of an optimized extended-release niacin formulation." *Int J Clin Pharmacol Ther* 45(2): 78-88.

Cooper, A., N, O'Flynn, et al. (2008). "Risk assessment and lipid modification for primary and secondary prevention of cardiovascular disease: summary of NICE guidance." *BMJ* 336(7655): 1246-1248.

Data Monitor (2008) "Strategic Perspectives: Adntdyslipidemics."

Dishy, V., F. Liu, et al. (2009). "Effects of Aspirin When Added to the Prostaglandin D2 Receptor Antagonist Laropiprant on Niacin-Induced Flushing Symptoms." *J Clin Pharmacol* 49(4): 416-422.

Duggal, J. K., M. Singh, et al. (2010). "Effect of Niacin Therapy on Cardiovascular Outcomes in Patients With Coronary Artery Disease." *Journal of Cardiovascular Pharmacology and Therapeutics* 15(2): 158-166.

Fleischman, A., S. E. Shoelson, et al. (2008). "Salsalate Improves Glycemia and Inflammatory Parameters in Obese Young Adults." *Diabetes Care* 31(2): 289-294.

Goldberg, A., P. Alagona, et al. (2000). "Multiple-dose efficacy and safety of an extended-release form of niacin in the management of hyperlipidemia." *The American journal of cardiology* 85(9): 1100-1105.

Goldberg, R. B. and T. A. Jacobson (2008). "Effects of Niacin on Glucose Control in Patients With Dyslipidemia." *Mayo Clinic Proceedings* 83(4): 470-478.

Goldfine, A. B., V. Fonseca, et al. (2010). "The Effects of Salsalate on Glycemic Control in Patients With Type 2 Diabetes." *Annals of Internal Medicine* 152(6): 346-357.

Goldfine, A. B., R. Silver, et al. (2008). "Use of Salsalate to Target Inflammation in the Treatment of Insulin Resistance and Type 2 Diabetes." *Clinical and Translational Science* 1(1): 36-43.

Gordon, D., J. Probstfield, et al. (1989). "High-density lipoprotein cholesterol and cardiovascular disease. Four prospective American studies." *Circulation* 79(1): 8-15.

Grundy, S. M., G. L. Vega, et al. (2002). "Efficacy, Safety, and Tolerability of Once-Daily Niacin for the Treatment of Dyslipidemia Associated With Type 2 Diabetes: Results of the Assessment of Diabetes Control and Evaluation of the Efficacy of Niaspan Trial." *Arch Intern Med* 162(14): 1568-1576.

Guyton, J., R. and P. Simmons, D. (2009). "Flushing and other dermatologic adverse events associated with extended-release niacin therapy." 3(2): 101-108.

Jackevicius, C. A., M. Mamdani, et al. (2002). "Adherence With Statin Therapy in Elderly Patients With and Without Acute Coronary Syndromes." *JAMA: The Journal of the American Medical Association* 288(4): 462-467.

Jacobson, T. A. (2010). "A "Hot" Topic in Dyslipidemia Management—"How to Beat a Flush": Optimizing Niacin Tolerability to Promote Long-term Treatment Adherence and Coronary Disease Prevention." *Mayo Clinic Proceedings* 85(4): 365-379.

Kashyap, M., L., M. McGovern, E., et al. (2002). "Long-term safety and efficacy of a once-daily niacin/lovastatin formulation for patients with dyslipidemia* *A complete list of participants in the Research Group and Publication Committee appears in the Appendix." *The American journal of cardiology* 89(6): 672-678.

Kastelein, J. J. P., S. I. van Leuven, et al. (2007). "Effect of Torcetrapib on Carotid Atherosclerosis in Familial Hypercholesterolemia." *N Engl J Med* 356(16): 1620-1630.

Knopp, R. H., P. Alagona, et al. (1998). "Equivalent efficacy of a time-release form of niacin (Niaspan) given once-a-night versus plain niacin in the management of hyperlipidemia." *Metabolism* 47(9): 1097-1104.

Knopp, R. H., B. M. Retzlaff, et al. (2009). "The SLIM Study: Slo-Niacin® and Atorvastatin Treatment of Lipoproteins and Inflammatory Markers in Combined Hyperlipidemia." *Journal of Clinical Lipidology* 3(3): 167-178.

Knopp, R. H., J. Ginsberg, et al. (1985). "Contrasting effects of unmodified and time-release forms of niacin on lipoproteins in hyperlipidemic subjects: Clues to mechanism of action of niacin." *Metabolism* 34(7): 642-650.

Kush, D., D. Y. Hu, et al. (2009). "Flushing Profile of Extended-Release Niacin/Laropiprant at Initiation of Therapy in Asian Lipid Clinic Patients." *Cardiology* 114(3): 192-198.

Lai, E., I. De Lepeleire, et al. (2007). "Suppression of Niacin-induced Vasodilation with an Antagonist to Prostaglandin D2 Receptor Subtype 1." *Clin Pharmacol Ther* 81(6): 849-857.

Maccubbin, D., H. E. Bays, et al. (2008). "Lipid-modifying efficacy and tolerability of extended-release niacin/laropiprant in patients with primary hypercholesterolaemia or mixed dyslipidaemia." *International Journal of Clinical Practice* 62(12): 1959-1970.

McKenney, J. (2004). "New Perspectives on the Use of Niacin in the Treatment of Lipid Disorders." *Arch Intern Med* 164(7): 697-705.

McKenney, J., H. Bays, et al. (2008). "SAFETY PROFILE OF EXTENDED-RELEASE NIACIN/LAROPIPRANT IN PATIENTS WITH DYSLIPIDEMIA." *Atherosclerosis Supplements* 9(1): 194-195.

McKenney, J., M., P. Jones, H., et al. (2007). "Comparative effects on lipid levels of combination therapy with a statin and extended-release niacin or ezetimibe versus a statin alone (the COMPELL study)." *Atherosclerosis* 192(2): 432-437.

McKenney, J. M., J. D. Proctor, et al. (1994). "A Comparison of the Efficacy and Toxic Effects of Sustained-vs Immediate-Release Niacin in Hypercholesterolemic Patients." *JAMA: The Journal of the American Medical Association* 271(9): 672-677

McQuaid, K., R. and L. Laine (2006). "Systematic Review and Meta-analysis of Adverse Events of Low-dose Aspirin and Clopidogrel in Randomized Controlled Trials." *The American journal of medicine* 119(8): 624-638.

Natarajan, P., K. K. Ray, et al. (2010). "High-Density Lipoprotein and Coronary Heart Disease: Current and Future Therapies." *J Am Coll Cardiol* 55(13): 1283-1299.

Nicholls, S. J., E. M. Tuzcu, et al. (2008). "Cholesteryl Ester Transfer Protein Inhibition, High-Density Lipoprotein Raising, and Progression of Coronary Atherosclerosis: Insights From ILLUSTRATE (Investigation of Lipid Level Management Using Coronary Ultrasound to Assess Reduction of Atherosclerosis by CETP Inhibition and HDL Elevation)." *Circulation* 118(24): 2506-2514.

Oberwittler, H. and M. Baccara-Dinet (2006). "Clinical evidence for use of acetyl salicylic acid in control of flushing related to nicotinic acid treatment." *International Journal of Clinical Practice* 60(6): 707-715.

Parhofer, K. G. (2009). "Review of extended-release niacin/laropiprant fixed combination in the treatment of mixed dyslipidemia and primary hypercholesterolemia." *Vascular Health and Risk Management* 5: 901-908.

Patrono, C., C. Baigent, et al. (2008). "Antiplatelet Drugs*." *Chest* 133(6 suppl): 199S-233S.

Shah, S., R. Ceska, et al. (2010). "Efficacy and safety of extended-release niacin/laropiprant plus statin vs. doubling the dose of statin in patients with primary hypercholesterolaemia or mixed dyslipidaemia." *International Journal of Clinical Practice* 64(6): 727-738.

Taylor, A. J., L. E. Sullenberger, et al. (2004). "Arterial Biology for the Investigation of the Treatment Effects of Reducing Cholesterol (ARBITER) 2: A Double-Blind, Placebo-Controlled Study of Extended-Release Niacin on Atherosclerosis Progression in Secondary Prevention Patients Treated With Statins." *Circulation* 110(23): 3512-3517.

Taylor, A. J., T. C. Villines, et al. (2009). "Extended-Release Niacin or Ezetimibe and Carotid Intima-Media Thickness." *N Engl J Med* 361(22): 2113-2122.

Thakkar, R. B., M. L. Kashyap, et al. (2009). "Acetylsalicylic Acid Reduces Niacin Extended-Release-Induced Flushing in Patients with Dyslipidemia." *American Journal of Cardiovascular Drugs* 9: 69-79.

The Coronary Drug Project Research Group (1975). "Clofibrate and Niacin in Coronary Heart Disease." *JAMA: The Journal of the American Medical Association* 231(4): 360-381.

The SEARCH Collaborative Group (2008). "SLCO1B1 Variants and Statin-Induced Myopathy—A Genomewide Study." *N Engl J Med* 359(8): 789-799.

Whitney, E. J., R. A. Krasuski, et al. (2005). "A Randomized Trial of a Strategy for Increasing High-Density Lipoprotein Cholesterol Levels: Effects on Progression of Coronary Heart Disease and Clinical Events." *Annals of Internal Medicine* 142(2): 95-104.

Wolfe, M., L., S. Vartanian, F., et al. (2001). "Safety and effectiveness of Niaspan when added sequentially to a statin for treatment of dyslipidemia." *The American journal of cardiology* 87(4): 476-479.

We claim:

1. A method of treating dyslipidemia and improving platelet aggregability, comprising administering to a patient in need thereof, an effective amount of isosorbide-2-acetylsalicylate-5-nicotinic acid (I):

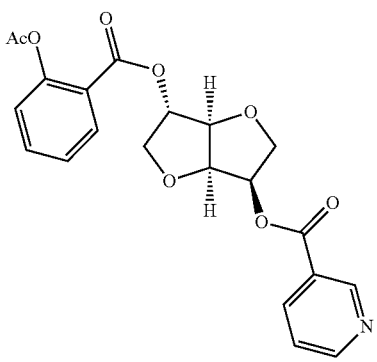

or a pharmaceutically acceptable salt thereof, wherein said method attenuates at least one of flushing, dys-glycemia, gastrointestinal and hepatotoxic side effects associated with nicotinic acid.

2. The method according to claim 1, further comprising the step of administering an additional therapeutic agent.

3. The method according to claim 2, wherein the additional therapeutic agent is a statin, a bile acid sequestrant, a fibric acid derivative or an ACE inhibitor.

4. The method according to claim 3, wherein the statin is selected from the group consisting of atorvastatin, fluvastatin, lovastatin, pravastatin, rosuvastatin and simvastatin.

5. The method according to claim 3, wherein the bile acid sequestrant is selected from the group consisting of colesevelam, cholestyramine and colestipol.

6. The method according to claim 3, wherein the fibric acid derivative is selected from the group consisting of gemfibrozil, fenofibrate and clofibrate.

7. The method according to claim 3, wherein the ACE inhibitor is selected from the group consisting of enalapril, captopril, zofenopril, ramipril, quinapril, perindopril, lisinopril, benazepril, moexipril, trandolapril and fosinopril.

8. A method of treating dyslipidemia comprising administering to a patient in need thereof, an effective amount of isosorbide-2-acetylsalicylate-5-nicotinic acid (I):

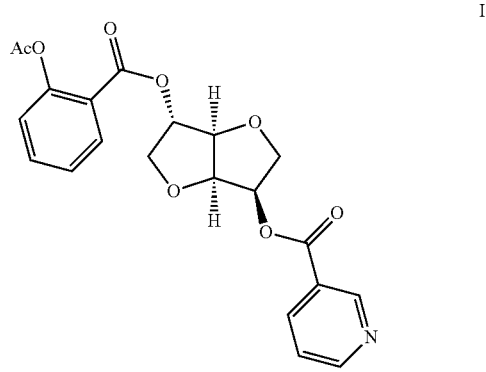 [SMILES: CC(=O)Oc1ccccc1C(=O)O[C@H]1CO[C@H]2[C@@H]1OC[C@H]2OC(=O)c1cccnc1]

or a pharmaceutically acceptable salt thereof, or a composition comprising isosorbide-2-acetylsalicylate-5-nicotinic acid or a pharmaceutically acceptable salt thereof.

9. The method according to claim 8, wherein the isosorbide-2-acetylsalicylate-5-nicotinic acid, or a pharmaceutically acceptable salt thereof, is formulated for delayed release of nicotinic acid.

10. The method according to claim 8, wherein the method does not result in gastrointestinal toxicity.

11. A method of decreasing LDL or TG levels and/or increase HDL levels in a biological sample comprising contacting said sample with isosorbide-2-acetylsalicylate-5-nicotinic acid (I):

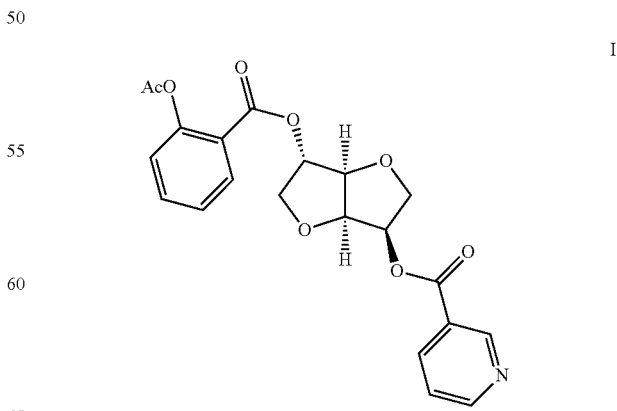

or a pharmaceutically acceptable salt thereof.

12. A method of decreasing LDL or TG levels in a patient comprising administering to said patient isosorbide-2-acetyl-salicylate-5-nicotinic acid (I):

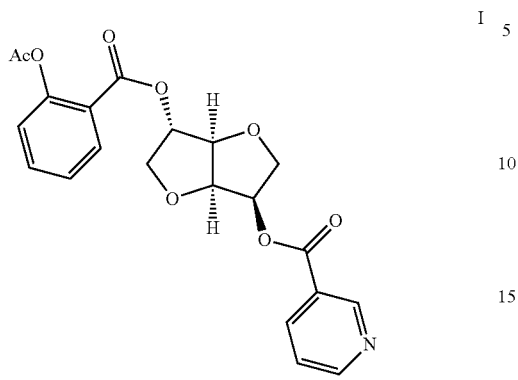

or a pharmaceutically acceptable salt thereof, or a composition comprising isosorbide-2-acetylsalicylate-5-nicotinic acid, or a pharmaceutically acceptable salt thereof.

13. The method according to claim 11, wherein said method increases HDL levels in the patient.

14. The method according to claim 12, wherein said method increases HDL levels in the patient, and/or decreases LDL and TG levels in the patient, but does not induce flushing.

15. The method according to claim 12, wherein said method increases HDL levels in the patient, and/or decreases LDL and TG levels in the patient, but does not induce hyperglycemia.

* * * * *

UNITED STATES PATENT AND TRADEMARK OFFICE
CERTIFICATE OF CORRECTION

PATENT NO. : 8,834,858 B2  
APPLICATION NO. : 13/175700  
DATED : September 16, 2014  
INVENTOR(S) : Mark Ledwidge et al.

Page 1 of 1

It is certified that error appears in the above-identified patent and that said Letters Patent is hereby corrected as shown below:

Title page, above "(51) Int. Cl.", please add:

Related U.S. Application Data

(60) Provisional application No. 61/361,337, filed on July 2, 2010.

Signed and Sealed this
Sixteenth Day of December, 2014

Michelle K. Lee
*Deputy Director of the United States Patent and Trademark Office*